United States Patent
Morishita et al.

(10) Patent No.: US 10,030,071 B2
(45) Date of Patent: Jul. 24, 2018

(54) ANTIBODY WHICH SPECIFICALLY REACTS WITH HUMAN INTEGRIN A6B4

(71) Applicants: UNIVERSITY OF MIYAZAKI, Mayazaki-shi, Miyazaki (JP); FUJITA HEALTH UNIVERSITY, Toyoake-shi, Aichi (JP); PERSEUS PROTEOMICS INC., Tokyo (JP)

(72) Inventors: Kazuhiro Morishita, Miyazaki-shi (JP); Kazuko Kaneda, Miyazaki-shi (JP); Yoshikazu Kurosawa, Toyoake-shi (JP); Gene Kurosawa, Tokyo (JP); Katsuyuki Mitomo, Tokyo (JP); Katsushi Kouda, Tokyo (JP); Yoshinori Ukai, Tokyo (JP)

(73) Assignees: UNIVERSITY OF MIYAZAKI, Miyazaki-shi, Miyazaki (JP); FUJITA HEALTH UNIVERSITY, Toyoake-shi, Aichi (JP); PERSEUS PROTEOMICS INC., Tokyo (JP)

( * ) Notice: Subject to any disclaimer, the term of this patent is extended or adjusted under 35 U.S.C. 154(b) by 53 days.

(21) Appl. No.: 14/916,943

(22) PCT Filed: Sep. 5, 2014

(86) PCT No.: PCT/JP2014/073507
§ 371 (c)(1),
(2) Date: Mar. 4, 2016

(87) PCT Pub. No.: WO2015/034052
PCT Pub. Date: Mar. 12, 2015

(65) Prior Publication Data
US 2016/0194400 A1 Jul. 7, 2016

(30) Foreign Application Priority Data
Sep. 5, 2013 (JP) ................. 2013-183703

(51) Int. Cl.
| | | |
|---|---|---|
| A61K 39/395 | (2006.01) | |
| C07K 16/00 | (2006.01) | |
| C07K 16/46 | (2006.01) | |
| C07K 16/28 | (2006.01) | |
| A61K 31/365 | (2006.01) | |
| A61K 31/704 | (2006.01) | |
| A61K 31/7068 | (2006.01) | |
| A61K 39/00 | (2006.01) | |

(52) U.S. Cl.
CPC ........ *C07K 16/2839* (2013.01); *A61K 31/365* (2013.01); *A61K 31/704* (2013.01); *A61K 31/7068* (2013.01); *A61K 39/3955* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/565* (2013.01); *C07K 2317/622* (2013.01); *C07K 2317/624* (2013.01); *C07K 2317/626* (2013.01); *C07K 2317/73* (2013.01); *C07K 2317/76* (2013.01); *C07K 2317/90* (2013.01); *C07K 2317/92* (2013.01); *C07K 2317/94* (2013.01); *C12N 2510/02* (2013.01)

(58) Field of Classification Search
None
See application file for complete search history.

(56) References Cited

U.S. PATENT DOCUMENTS

| | | |
|---|---|---|
| 5,530,101 A | 6/1996 | Queen et al. |
| 5,585,089 A | 12/1996 | Queen et al. |
| 5,693,761 A | 12/1997 | Queen et al. |
| 5,693,792 A | 12/1997 | Torii et al. |
| 5,714,350 A | 2/1998 | Co et al. |
| 5,777,085 A | 7/1998 | Co et al. |
| 6,018,032 A | 1/2000 | Koike et al. |
| 6,538,111 B1 | 3/2003 | Koike et al. |
| 7,179,464 B2 | 2/2007 | Koike et al. |
| 7,238,354 B2 | 7/2007 | Koike et al. |

(Continued)

FOREIGN PATENT DOCUMENTS

| | | |
|---|---|---|
| JP | 2005-185281 A | 7/2005 |
| JP | 4870348 B2 | 2/2012 |

(Continued)

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. 2002, Jul. 5, 320(2):415-28. (Year: 2002).*
Kennel et al. Second Generation Monoclonal Antibodies to the Human Integrin α6β4. Hybridoma. 9(3):243-255, 1990 (Year: 1990).*
Gabarra et al. Antibodies directed to α6β4 highlight the adhesive and signaling functions of the integrin in breast cancer cell lines. Cancer Biology & Therapy. 9:6, 437-445; Mar. 15, 2010. (Year: 2010).*

(Continued)

*Primary Examiner* — Maher M Haddad
(74) *Attorney, Agent, or Firm* — Birch, Stewart, Kolasch & Birch, LLP

(57) ABSTRACT

It is an object of the present invention to provide an anti-ITGA6/B4 human antibody, which specifically recognizes ITGA6B4 complex expressed on a cell membrane and inhibits the adhesion of the ITGA6B4 complex to laminin, so as to inhibit adhesion of cancer cells to a bone marrow niche, and which is also capable of remarkably enhancing the effects of an anticancer agent on an anticancer agent resistant strain. The present invention provides an antibody against integrin A6B4, wherein the antibody specifically recognizes a human integrin A6B4 complex and inhibits intercellular adhesion.

5 Claims, 11 Drawing Sheets
(4 of 11 Drawing Sheet(s) Filed in Color)

(56) References Cited

U.S. PATENT DOCUMENTS

| | | | |
|---|---|---|---|
| 2003/0096977 | A1 | 5/2003 | Koike et al. |
| 2005/0272918 | A1 | 12/2005 | Koike et al. |
| 2007/0046304 | A1 | 3/2007 | Koike et al. |
| 2008/0057063 | A1 | 3/2008 | Rinkenberger et al. |
| 2008/0317752 | A1* | 12/2008 | Giancotti ........... C07K 16/2839 424/138.1 |
| 2009/0053243 | A1 | 2/2009 | Kurosawa et al. |
| 2009/0203538 | A1 | 8/2009 | Sugioka et al. |
| 2012/0045773 | A1* | 2/2012 | Morishita ........... A61K 31/7088 435/7.1 |
| 2012/0046451 | A1 | 2/2012 | Kurosawa et al. |
| 2014/0235833 | A1 | 8/2014 | Sugioka et al. |

FOREIGN PATENT DOCUMENTS

| | | |
|---|---|---|
| WO | WO 92/01047 A1 | 1/1992 |
| WO | WO 92/02190 A1 | 2/1992 |
| WO | WO 92/20791 A1 | 11/1992 |
| WO | WO 93/06213 A1 | 4/1993 |
| WO | WO 93/11235 A1 | 6/1993 |
| WO | WO 93/19172 A1 | 9/1993 |
| WO | WO 95/01438 A1 | 1/1995 |
| WO | WO 95/15388 A1 | 6/1995 |
| WO | WO 97/10354 A1 | 3/1997 |
| WO | WO 2006/090750 A1 | 8/2006 |
| WO | WO2006111925 * | 10/2006 |
| WO | WO 2008/007648 A1 | 1/2008 |
| WO | WO 2008/127655 A1 | 10/2008 |
| WO | WO 2010/098186 A1 | 9/2010 |

OTHER PUBLICATIONS

Hintermann et al. Inhibitory Role of α6β4-Associated Erbb-2 and Phosphoinositide 3-Kinase in Keratinocyte Haptotactic Migration Dependent on α3β1 Integrin. J Cell Biol. Apr. 30, 2011; 153(3): 465-478.*

Yamakawa et al. The Increased Expression of Integrin a6 (ITGA6) Enhances Drug Resistance in EVI1high Leukemia. PLoS One 7(1): e30706. doi:10.1371/journal.pone.0030706 (Year: 2012).*

Ishikawa et al., Chemotherapy-resistant human AML stem cells home to and engraft within the bone-marrow endosteal region. Nature Biotechnology 25, 1315-1321 (2007).*

Isaac Rabinovitz and Arthur M. Mercurio. The integrin alpha6beta4 functions in carcinoma cell migration on laminin-1 by mediating the formation and stabilization of actin-containing motility structures. J Cell Biol. Dec. 29, 1997; 139(7):1873-84. (Year: 1997).*

Huang et al. α6β1 and α6 β4 integrins and their critical role in promoting resistance to multiple treatment strategies for breast cancer . The Charles A. Coltman. Jr. San Antonio Breast Cancer Symposium . Dec. 13-16, 2007. Abstract # 4113 (Year: 2007).*

Felgner et al., "Lipofection: A Highly Efficient, Lipid-mediated DNA-transfection Procedure," Proc. Natl. Acad. Sci., vol. 84, Nov. 1987, pp. 7413-7417.

Graham et al., "A New Technique for the Assay of Infectivity of Human Adenovirus 5 DNA," Virology, vol. 52, 1973, pp. 456-467.

Hashimoto-Gotoh et al., "An Oligodeoxyribonucleotide-directed Dual Amber Method for Site-directed Mutagenesis," Gene, vol. 152, 1995, pp. 271-275.

Hu et al., "Establishment and Characterization of Two Novel Cytokine-responsive Acute Myeloid and Monocytic Leukemia Cell Lines, MUTZ-2 and MUTZ-3," Leukemia, vol. 10, 1996, pp. 1025-1040.

International Preliminary Report on Patentability and Written Opinion of the International Searching Authority (forms PCT/IB/373, PCT/ISA/237, PCT/IB/336 and PCT/IB/326), dated Mar. 17, 2016, for International Application No. PCT/JP2014/073507, along with English translations.

International Search Report (forms PCT/ISA/210 and PCT/ISA/220), dated Dec. 9, 2014 for International Application No. PCT/JP2014/073507, along with an English translation.

Junghans et al., "Anti-Tac-H, a Humanized Antibody to the Interleukin 2 Receptor with New Features for Immunotherapy in Malignant and Immune Disorders," Cancer Research, vol. 50, Mar. 1, 1990, pp. 1495-1502 (Total 9 pages).

Kramer et al., "Oligonucleotide-Directed Construction of Mutations via Gapped Duplex DNA," Methods in Enzymology, vol. 154, 1987, pp. 350-367.

Kramer et al., "The Gapped Duplex DNA Approach to Oligonucleotide-directed Mutation Construction," Nucleic Acids Research, vol. 12, No. 24, 1984, pp. 9441-9456 (Total 16 pages).

Kunkel et al., "Rapid and Efficient Site-specific Mutagenesis without Phenotypic Selection," Proc. Natl. Acad. Sci., vol. 82, Jan. 1985, pp. 488-492.

Kurosawa et al., "Comprehensive Screening for Antigens Overexpressed on Carcinomas-via Isolation of Human mAbs that may be Therapeutic," PNAS, vol. 105, No. 20, May 20, 2008, pp. 7287-7292.

Mangoo-Karim et al., "Renal Epithelial Cyst Formation and Enlargement in Vitro: Dependence on cAMP," Proc. Natl. Acad. Sci., vol. 86, Aug. 1989, pp. 6007-6011.

Matsunaga et al. "Interaction Between Leukemic-cell VLA-4 and Stromal Fibronectin is a Decisive Factor for Minimal Residual Disease of Acute Myelogenous Leukemia," Nature Medicine, vol. 9, No. 9, Sep. 2003 (Published online Aug. 3, 2003), pp. 1158-1165 and vol. 11, No. 5, May 2005, pp. 578.

Motmans et al., "Immunotherapy for Cancer: Construction, Expression and Functional Characterization of Chimeric Antibodies," European Journal of Cancer Prevention, vol. 5, 1996, pp. 512-519.

Oval et al., "Characterization of a Factor-Dependent Acute Leukemia Cell Line With Translocation (3;3)(q21;q26)," Blood, vol. 76, No. 7, Oct. 1, 1990, pp. 1369-1374 (Total 7 pages).

Rabinovitz et al., "The Integrin α6β4 Functions in Carcinoma Cell Migration on Laminin-1 by Mediating the Formation and Stabilization of Actin-containing Motility Structures," The Journal of Cell Biology, vol. 139, No. 7, Dec. 29, 1997, pp. 1873-1884.

Taetle et al., "Effects of Transforming Growth Factor β1on Growth and Apoptosis of Human Acute Myelogenous Leukemia Cells," Cancer Research, vol. 53, Jul. 15, 1993, pp. 3386-3393 (Total 9 pages).

Wright et al., "Effect of C2-Associated Carbohydrate Structure on Ig Effector Function: Studies with Chimeric Mouse-Human IgG1 Antibodies in Glycosylation Mutants of Chinese Hamster Ovary Cells," The Journal of Immunology, vol. 160, 1998, pp. 3393-3402 (Total 11 pages).

Yamakawa et al., "The Increased Expression of Integrin α6 (ITGA6) Enhances Drug Resistance in EVI1high Leukemia," PLoS One, vol. 7, Issue 1, e30706, Jan. 2012, pp. 1-13.

Zoller et al., "Oligonucleotide-Directed Mutagenesis of DNA Fragments Cloned into MI3 .Vectors," Methods in Enzymology, vol. 100, 1983, pp. 468-500.

Extended European Search Report, dated Feb. 10, 2017, for corresponding European Application No. 14842086.2.

Japanese Office Action issued in Japanese Patent Application No. 2015-535531 dated Jun. 12, 2018.

* cited by examiner

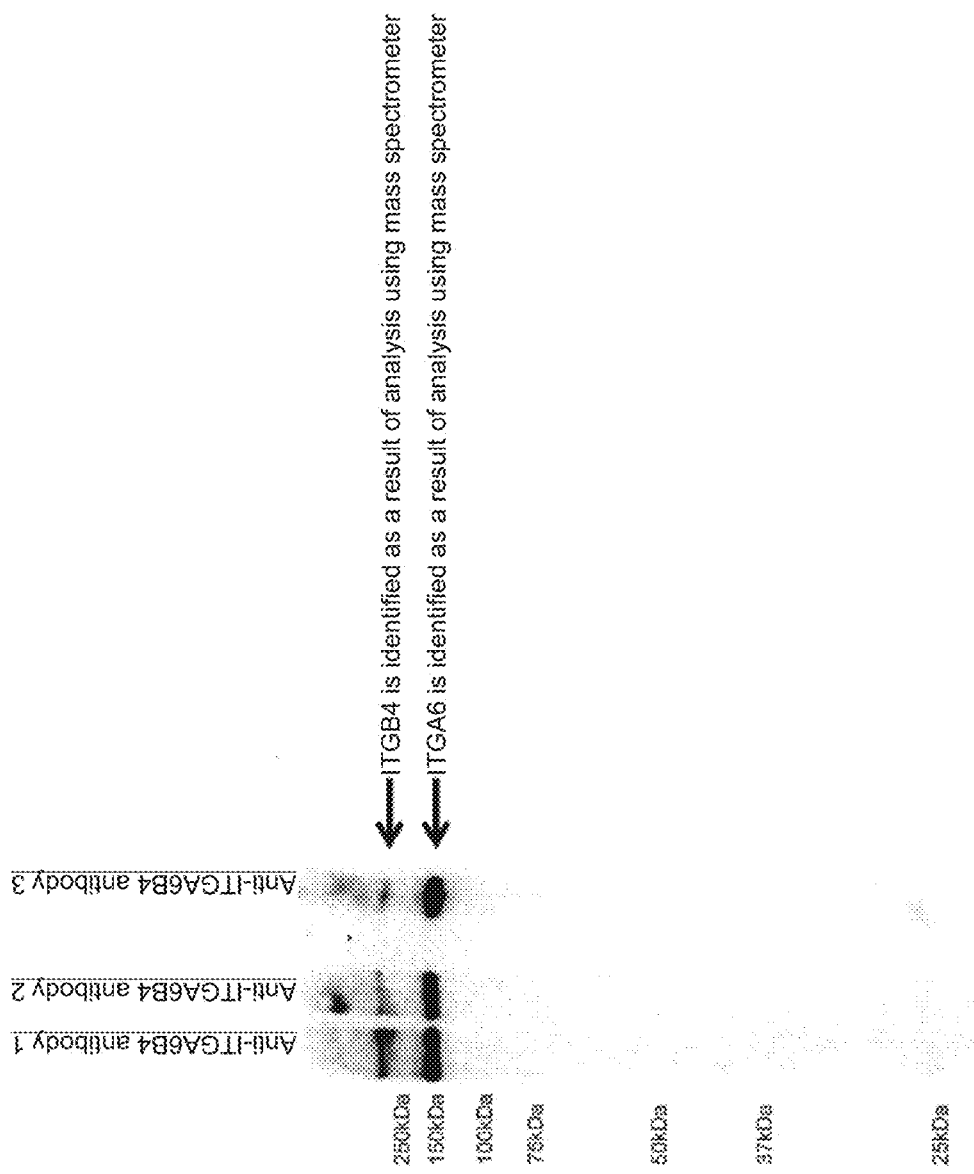

[Figure 2]

Results 1 obtained by mass spectrometry of purification bands obtained as a result of IP using anti-ITGA6B4 antibody 1 and PC14 cell lysate

[Figure 3]

Results 2 obtained by mass spectrometry of purification bands obtained as a result of IP using anti-ITGA6B4 antibody 1 and PC14 cell lysate

(MATRIX SCIENCE) Mascot Search Results

[Figure 4]
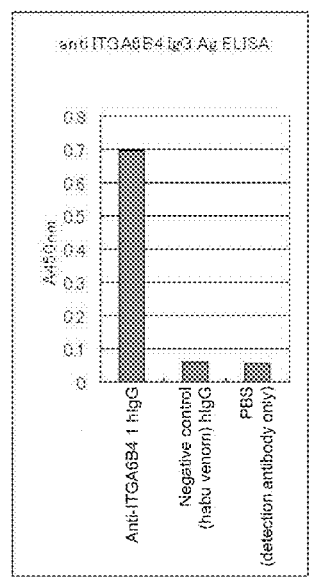

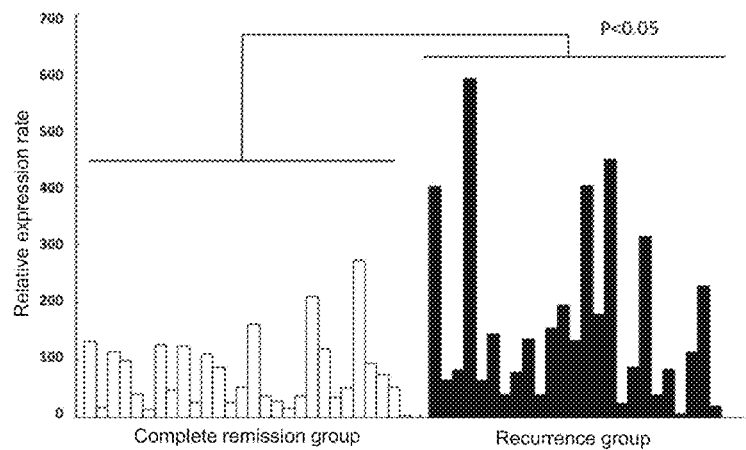
[Figure 5]

[Figure 6]
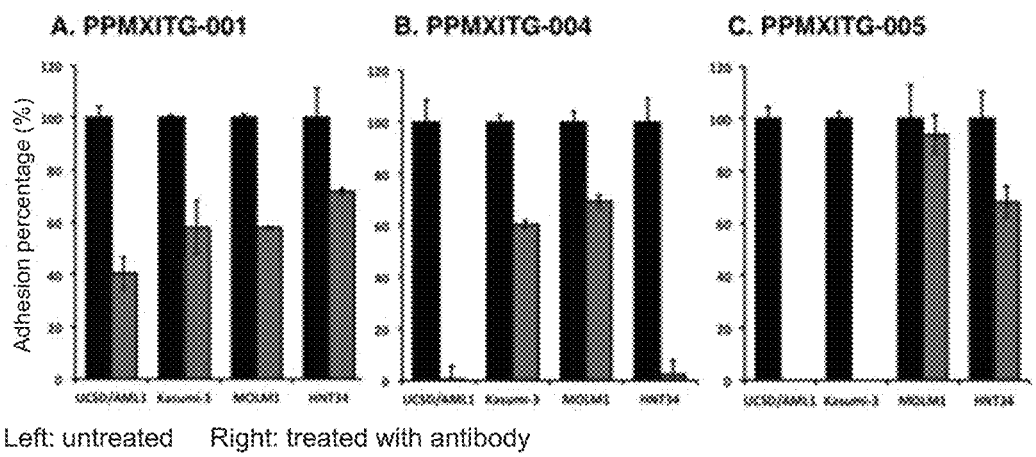
Left: untreated    Right: treated with antibody
[Figure 7]
Inhibitory effect was calculated by setting the number of untreated cells adhered as 100.
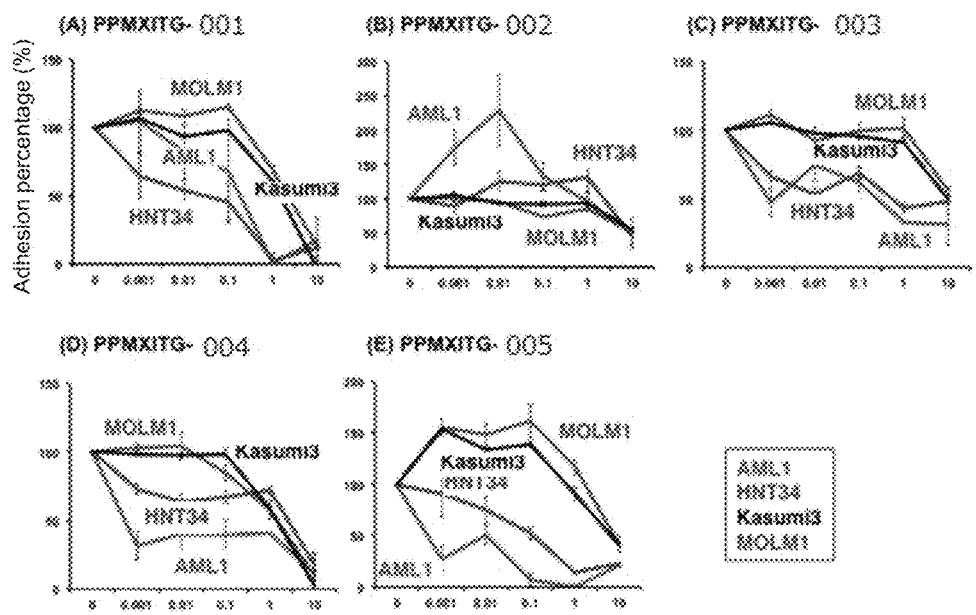

Combined effects with anticancer agents

List of combined results with anticancer agents

[Figure 9]
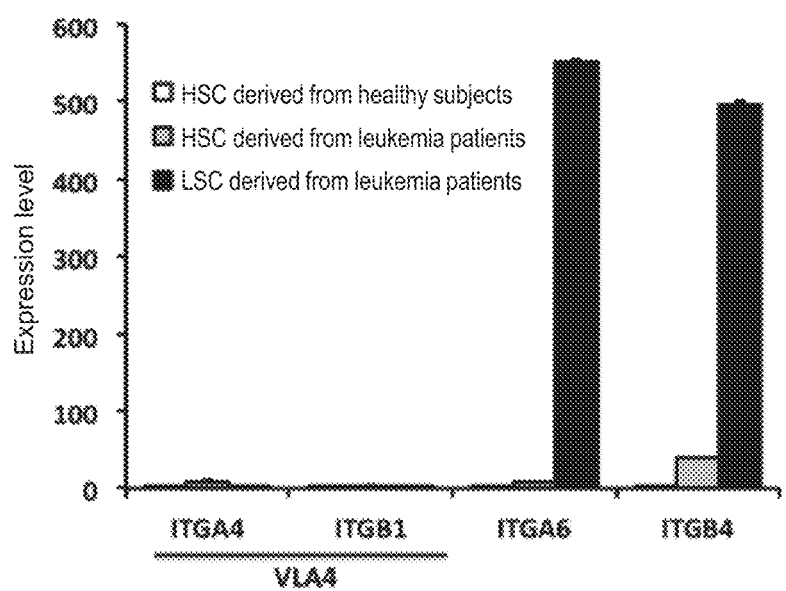

[Figure 10]
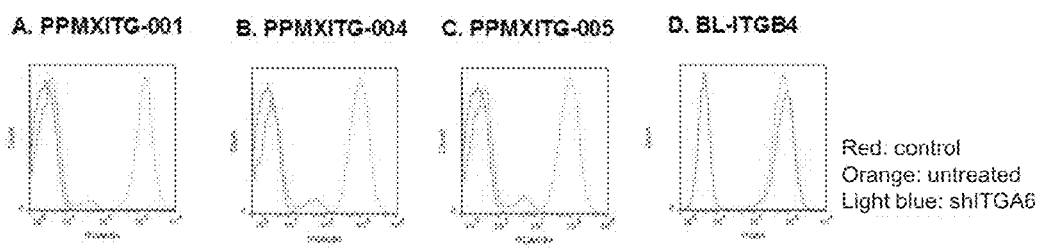
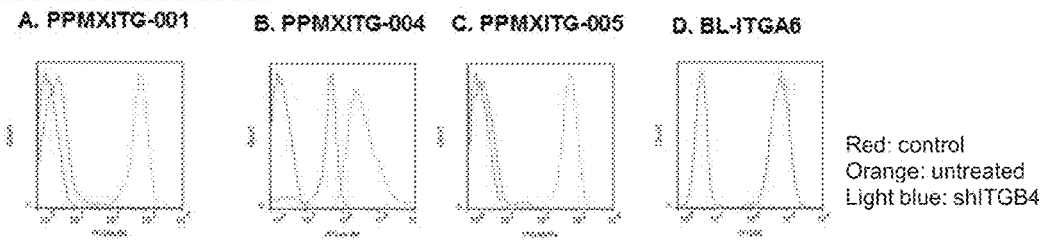

|  | ITG001 | ITG002 | ITG003 | ITG004 | ITG005 | ITG006 | ITG007 | ITG008 | ITG009 | ITG010 | ITG011 | ITG012 | ITG013 | ITG014 | PBS |
|---|---|---|---|---|---|---|---|---|---|---|---|---|---|---|---|
| AML1 | 107 | 106 | 96 | 104 | 86 | 101 | 94 | 86 | 94 | 97 | 95 | 94 | 89 | 86 | 100 |
| SW480 | 100 | 113 | 88 | 89 | 90 | 96 | 96 | 103 | 99 | 104 | 100 | 116 | 86 | 93 | 100 |

[Figure 13]
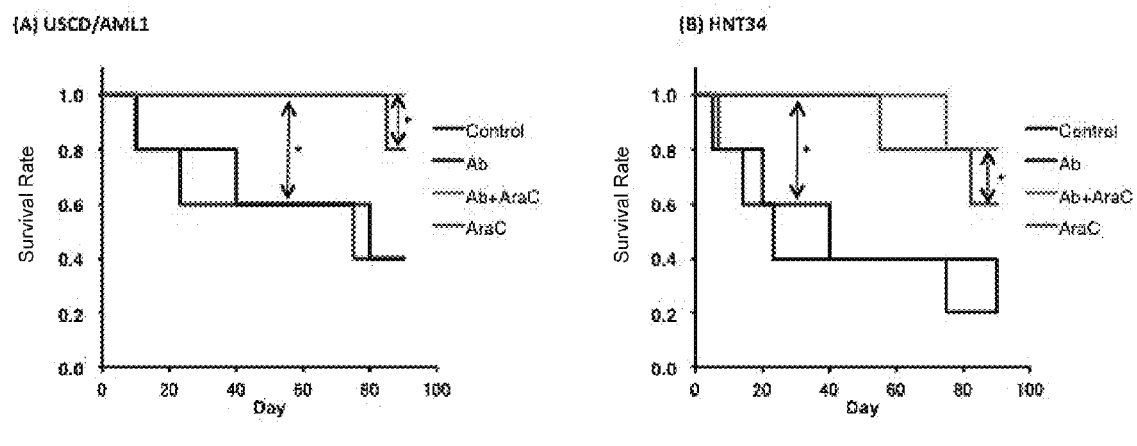

```
                              SEQUENCE LISTING

<160> NUMBER OF SEQ ID NOS: 31

<210> SEQ ID NO 1
<211> LENGTH: 5
<212> TYPE: PRT
<213> ORGANISM: Human

<400> SEQUENCE: 1

Asp Tyr Tyr Met Ser
1               5

<210> SEQ ID NO 2
<211> LENGTH: 17
<212> TYPE: PRT
<213> ORGANISM: Human

<400> SEQUENCE: 2

Tyr Ile Ser Ser Ser Gly Ser Thr Ile Tyr Tyr Ala Asp Ser Val Lys
1               5                   10                  15

Gly

<210> SEQ ID NO 3
<211> LENGTH: 10
<212> TYPE: PRT
<213> ORGANISM: Human

<400> SEQUENCE: 3

Trp Asp Thr Ala Met Ala Thr Phe Asp Tyr
1               5                   10

<210> SEQ ID NO 4
<211> LENGTH: 13
<212> TYPE: PRT
<213> ORGANISM: Human

<400> SEQUENCE: 4

Ser Gly Ser Ser Ser Asn Ile Gly Asn Ser Tyr Val Ser
1               5                   10

<210> SEQ ID NO 5
<211> LENGTH: 7
<212> TYPE: PRT
<213> ORGANISM: Human

<400> SEQUENCE: 5

Asp Asn Asn Lys Arg Pro Ser
1               5

<210> SEQ ID NO 6
<211> LENGTH: 11
<212> TYPE: PRT
<213> ORGANISM: Human

<400> SEQUENCE: 6

Gly Thr Trp Asp Ser Ser Leu Ser Ala Tyr Val
1               5                   10

<210> SEQ ID NO 7
<211> LENGTH: 5
<212> TYPE: PRT
```

```
<213> ORGANISM: Human

<400> SEQUENCE: 7

Ser Tyr Ala Ile Ser
1               5

<210> SEQ ID NO 8
<211> LENGTH: 17
<212> TYPE: PRT
<213> ORGANISM: Human

<400> SEQUENCE: 8

Gly Ile Ile Pro Thr Phe Gly Thr Ala Asn Tyr Ala Gln Lys Phe Gln
1               5                   10                  15

Gly

<210> SEQ ID NO 9
<211> LENGTH: 13
<212> TYPE: PRT
<213> ORGANISM: Human

<400> SEQUENCE: 9

Ser Thr Gly Tyr Tyr Tyr Tyr Tyr Gly Met Asp Val
1               5                   10

<210> SEQ ID NO 10
<211> LENGTH: 11
<212> TYPE: PRT
<213> ORGANISM: Human

<400> SEQUENCE: 10

Arg Ala Ser Gln Ser Ile Ser Ser Tyr Leu Asn
1               5                   10

<210> SEQ ID NO 11
<211> LENGTH: 7
<212> TYPE: PRT
<213> ORGANISM: Human

<400> SEQUENCE: 11

Ala Ala Ser Ser Leu Gln Ser
1               5

<210> SEQ ID NO 12
<211> LENGTH: 9
<212> TYPE: PRT
<213> ORGANISM: Human

<400> SEQUENCE: 12

Gln Gln Ser Tyr Ser Thr Pro Phe Thr
1               5

<210> SEQ ID NO 13
<211> LENGTH: 5
<212> TYPE: PRT
<213> ORGANISM: Human

<400> SEQUENCE: 13

Ser His Tyr Ile Asn
1               5

<210> SEQ ID NO 14
<211> LENGTH: 16
<212> TYPE: PRT
```

```
<213> ORGANISM: Human

<400> SEQUENCE: 14

Val Ile Tyr Ser Gly Gly Gly Thr Tyr Tyr Ala Asp Ser Val Arg Gly
1               5                   10                  15

<210> SEQ ID NO 15
<211> LENGTH: 6
<212> TYPE: PRT
<213> ORGANISM: Human

<400> SEQUENCE: 15

Gly Gly Gly Leu Asp Val
1               5

<210> SEQ ID NO 16
<211> LENGTH: 14
<212> TYPE: PRT
<213> ORGANISM: Human

<400> SEQUENCE: 16

Thr Leu Arg Ser Asp Val Asn Val Gly Thr Tyr Lys Ile Tyr
1               5                   10

<210> SEQ ID NO 17
<211> LENGTH: 11
<212> TYPE: PRT
<213> ORGANISM: Human

<400> SEQUENCE: 17

Tyr Asn Ser Asp Ser Asp Lys Gln Gln Gly Ser
1               5                   10

<210> SEQ ID NO 18
<211> LENGTH: 11
<212> TYPE: PRT
<213> ORGANISM: Human

<400> SEQUENCE: 18

Tyr Cys Met Ile Arg His Asn Ser Ala Trp Val
1               5                   10

<210> SEQ ID NO 19
<211> LENGTH: 5
<212> TYPE: PRT
<213> ORGANISM: Human

<400> SEQUENCE: 19

Gly Tyr Tyr Met His
1               5

<210> SEQ ID NO 20
<211> LENGTH: 17
<212> TYPE: PRT
<213> ORGANISM: Human

<400> SEQUENCE: 20

Ile Ile Asn Pro Ser Gly Gly Thr Thr Arg Leu Ala Gln Lys Phe Gln
1               5                   10                  15

Gly

<210> SEQ ID NO 21
<211> LENGTH: 12
<212> TYPE: PRT
```

```
<213> ORGANISM: Human

<400> SEQUENCE: 21

Glu Ala His Ser Ser Gly Ser Tyr Phe Phe Asp Tyr
1               5                   10

<210> SEQ ID NO 22
<211> LENGTH: 11
<212> TYPE: PRT
<213> ORGANISM: Human

<400> SEQUENCE: 22

Arg Ala Ser Gln Ser Ile Ser Thr Trp Leu Ala
1               5                   10

<210> SEQ ID NO 23
<211> LENGTH: 7
<212> TYPE: PRT
<213> ORGANISM: Human

<400> SEQUENCE: 23

Gln Ala Ser Thr Leu Thr Ser
1               5

<210> SEQ ID NO 24
<211> LENGTH: 10
<212> TYPE: PRT
<213> ORGANISM: Human

<400> SEQUENCE: 24

Gln Glu Tyr Asn Ser Tyr Ser Pro Trp Ala
1               5                   10

<210> SEQ ID NO 25
<211> LENGTH: 5
<212> TYPE: PRT
<213> ORGANISM: Human

<400> SEQUENCE: 25

Asp Tyr Ala Met His
1               5

<210> SEQ ID NO 26
<211> LENGTH: 17
<212> TYPE: PRT
<213> ORGANISM: Human

<400> SEQUENCE: 26

Gly Ile Ser Trp Asn Ser Gly Ser Ile Gly Tyr Ala Asp Ser Val Lys
1               5                   10                  15

Gly

<210> SEQ ID NO 27
<211> LENGTH: 13
<212> TYPE: PRT
<213> ORGANISM: Human

<400> SEQUENCE: 27

Ala Leu Pro Ser Gly Gly Trp Ala Asp Ala Phe Asp Ile
1               5                   10

<210> SEQ ID NO 28
<211> LENGTH: 13
<212> TYPE: PRT
```

```
<213> ORGANISM: Human

<400> SEQUENCE: 28

Thr Arg Ser Ser Gly Ser Ile Ala Ser Asn Tyr Val Gln
1               5                   10

<210> SEQ ID NO 29
<211> LENGTH: 7
<212> TYPE: PRT
<213> ORGANISM: Human

<400> SEQUENCE: 29

Glu Asp Asp Gln Arg Pro Ser
1               5

<210> SEQ ID NO 30
<211> LENGTH: 9
<212> TYPE: PRT
<213> ORGANISM: Human

<400> SEQUENCE: 30

Gln Ser Phe His Asp Thr Lys Gln Met
1               5

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: linker

<400> SEQUENCE: 31

Gly Gly Gly Gly Ser Gly Gly Gly Gly Ser Gly Gly Gly Gly Ser
1               5                   10                  15
```

ANTIBODY WHICH SPECIFICALLY REACTS WITH HUMAN INTEGRIN A6B4

TECHNICAL FIELD

The present invention relates to an antibody which specifically reacts with human integrin A6B4.

BACKGROUND ART

More than half the adult acute myeloid leukemia (AML) exhibits resistance to chemotherapy using anticancer agents, and thus, is refractory. Such refractory leukemia has poor prognosis, even if born marrow transplantation has been conducted. Thus, it is urgently required to develop a novel treatment method therefor. To date, in order to clarify a mechanism of the onset of refractory leukemia, the present inventors had conducted genomic analysis and the functional analysis of onset factors thereof, and had isolated a large number of onset-related factor groups. In particular, the inventors had conducted the pathological analysis of refractory leukemia involving an overexpression of the transcriptional factor EVIL and as a result of comprehensive gene expression analysis, they had identified an overexpression of α6-integrin (ITGA6) and β4 (ITGB4). It had been found that this ITGA6/B4 is highly expressed not only in leukemia involving an overexpression of EVI1, but also in a group of patients with leukemia relapse after completion of the treatment. This phenomenon is generally observed over the refractory leukemia as a whole. Moreover, it had also been identified that the overexpression of ITGA6/B4 contributes to the enhanced adhesion of leukemia cells to osteoblasts and laminin as an extracellular matrix, and further, to the achievement of resistance to various types of anticancer agents (Non Patent Literature 1).

The enhanced cell adhesion ability of leukemia cells is a phenomenon that has been well known as Cell Adhesion Mediated Drug Resistance (CAM-DR), and in recent years, a mechanism whereby leukemic stem cells (hereinafter referred to as "LSC") take over a bone marrow niche (hereinafter referred to as "osteoblasts) for hematopoietic stem cells (hereinafter referred to as "HSC") (which is adhesion involving utilization of a bone marrow niche environment), and achieve resistance to anticancer agents, has been revealed. An integrin family associated with adhesion of HSC to the bone marrow niche has is mainly VLA-4 (ITGA4/B1) (Non Patent Literature 2), but it has been found that LSC depends on ITGA6B4. Accordingly, it is considered that the development of a treatment method, which targets a specific adhesion molecule ITGA6/B4 that is associated with CAM-DR leading to incurability, would lead to the development of a method for effectively treating refractory leukemia, for which there have been no conventional treatment methods so far (Patent Literature 1).

An antibody capable of reacting against ITGA6B4 has been manufactured by Biogen IDEC MA, Inc., and has been reported in 2007. This antibody has been reported to have an ability to inhibit the growth of cells and inhibit adhesion of the cells to laminin (Patent Literature 2).

The present inventors have searched for an antigen (antibody) specific to cancer cells by a method for comprehensively isolating a human antibody, which targets many cancer cells, based on the Phage Display method (Patent Literature 3). As a result, ITGA6/B4 (antibody) has been included in the obtained 29 types of targets, and the validity of ITGA6/B4 as an antibody drug target has been proved also from another viewpoint (Non Patent Literature 3).

From the viewpoint of the side effects of a pharmaceutical product, since chemotherapeutic agents are not specific to cancer cells, but also exhibit effects on cells with activated cellular division, including normal cells, it has been conventionally very important to control administration of the agents. On the other hand, since molecular-targeted agents have been selectively designed to specific targeted molecules, these agents are characterized in that their side effects are reduced in comparison to the aforementioned chemotherapeutic agents. Antibodies are also molecular-targeted agents, and thus, when compared with enzyme inhibitors (kinase inhibitors) and the like, the specificity of such antibodies to targets has been improved. With such target specificity, antibody drugs are anticipated to have reduced side effects, but individual antibody drugs are observed to have characteristic side effects. It is considered that some side effects are caused by induction of immune responses such as ADCC (antibody-dependent cellular cytotoxicity) or CDC (complement-dependent cytotoxicity), which are derived from the properties of antibody molecules, and that some other side effects are caused by agonistic or antagonistic activities induced as a result of action on target molecules. Moreover, in recent years, antibody drugs have exhibited strong effects as a result of reinforced immune responses or drug modification. At the same time, however, considerable attention should be paid on the side effects of the antibody drugs.

PRIOR ART LITERATURES

Patent Literatures

Patent Literature 1: WO2010/098166
Patent Literature 2: WO2008/127655
Patent Literature 3: Japanese Patent No. 4870348

Non Patent Literatures

Non Patent Literature 1: The Increased Expression of Integrin α6 (ITGA6) Enhances Drug Resistance in EVI1$^{high}$ Leukemia, Yamakawa, N., et al., ProsOne Vol. 7 Issue 1 e30706 (2012)
Non Patent Literature 2: Interaction between leukemic-cell VLA-4 and stromal fibronectin is a decisive factor for minimal residual disease of acute myelogenous leukemia. Matsunaga, T., et al., Nat Med; 9: 1158-65. (2003)
Non Patent Literature 3: Comprehensive screening for antigens overexpressed on carcinomas via isolation of human mAbs that may be therapeutic, Kurosawa G et al., Proc Nat Acad Sci USA 105, 7287-7292 <2008>

SUMMARY OF INVENTION

Object to be Solved by the Invention

It is an object of the present invention to provide an anti-ITGA6B4 human antibody, which specifically recognizes an integrin A6B4 (ITGA6B4) complex expressed on a cell membrane and inhibits the adhesion of the ITGA6B4 complex to laminin, so as to inhibit adhesion of cancer cells to a bone marrow niche, and which is also capable of remarkably enhancing the effects of an anticancer agent on an anticancer agent resistant strain. In addition, it is another object of the present invention to provide an inhibitor of cancer cell adhesion and a pharmaceutical composition, each of which comprises the above-described anti-ITGA6/B4 human antibody with a few side effects upon the use thereof.

Means for Solving the Object

The present inventors have conducted intensive studies directed towards achieving the above-described objects. The inventors have focused on the fact that refractory leukemic stem cells adhere to a bone marrow niche so as to obtain resistance to anticancer agents, and they have assumed that the effects of anticancer agents can be improved by inhibiting stable adhesion of the stem cells to the bone marrow niche, thereby releasing the stem cells or inhibiting the adhesion thereof to the niche (this phenomenon is referred to as "turn out"). Based on the concept that antibody molecules would be useful for turning refractory leukemic stem cells out of a niche, the inventors have searched for an antibody having an activity of recognizing a human integrin A6B4 complex and inhibiting adhesion of cancer cells to a niche, so as to increase the sensitivity of the cancer cells to anticancer agents.

The present inventors have established a method for isolating a complete human antibody against an intact protein on the surface of a cell, which is based on the phage display method. Since this method uses a phage library retaining an enormous repertoire, it has a high variety of antibodies. In addition, since this method can directly screen cancer cells, even an antibody against a complex protein on the cell surface can be easily obtained by this method. In the present invention, by applying this method, a plurality of antibodies against an ITGA6B4 complex expressed on a cancer cell membrane has been obtained. Thereafter, antibodies exhibiting cancer specificity, which react with a large number of cancer cells, including leukemic stem cells, kidney cancer cells, lung cancer cells, etc., have been selected. Thereafter, complete human IgG antibodies have been produced from the obtained antibodies according to a DNA recombination technique.

Subsequently, based on the idea that since refractory leukemic stem cells adhere to a bone marrow niche to obtain resistance to anticancer agents, the effects of the anticancer agents can be improved by "turning the stem cells out of" the bone marrow niche, and that antibodies are useful for such "turning the stem cells out of" the niche, the present inventors have conceived of a "turn-out treatment" of using antibodies. In the case of this treatment, mainly necessary medicinal effect is inhibition of adhesion of the stem cells to the bone marrow, and there is a fear that other auxiliary effects would cause unexpected action on all cells that express ITGA6B4. Hence, in the present invention, an anti-ITGA6BA antibody, which does not affect the growth of cells, has been selected. Based on the aforementioned thought, the present inventors have conducted basic studies regarding the "turn-out treatment," using a human antibody. As a result, the inventors have succeeded in confirming, using a model system, that the anti-ITGA6B4 antibody of the present invention is able to inhibit adhesion of leukemic stem cells to a bone marrow niche, and that an antibody having an adhesion-inhibiting action reduces the resistance of the cancer cells to anticancer agents, thereby completing the present invention.

The present invention provides the following invention.
(1) An antibody against integrin A6B4, wherein the antibody specifically recognizes a human integrin A6B4 complex and inhibits intercellular adhesion.
(2) An antibody against integrin A6B4, wherein the antibody specifically recognizes a human integrin A6B4 complex and increases a sensitivity of a cancer cell expressing a target antigen to an anticancer agent.
(3) The antibody according to (1) or (2), which does not substantially have an influence on the growth of the cell.
(4) An antibody against integrin A6B4, wherein the antibody specifically recognizes a human integrin A6B4 complex and has at least two or more of the following (a) to (c):
(a) an ability to inhibit intercellular adhesion mediated by integrin A6B4;
(b) an ability to increase a sensitivity of a cancer cell to an anticancer agent; and
(c) a property of substantially not having an influence on growth of cell.
(5) The antibody according to (2) or (4), wherein the anticancer agent is selected from the following (i) to (v):
(i) an alkylating agent selected from among ifosfamide, nimustine hydrochloride, procarbazine hydrochloride, cyclophosphamide, dacarbazine and thiotepa;
(ii) a metabolic antagonist selected from among cytarabine, enocitabine, gemcitabine hydrochloride, carmofur, tegafur and fluorouracil;
(iii) a plant alkaloid selected from among etoposide, irinotecan, docetaxel, paclitaxel, vincristine, vindesine and vinblastine;
(iv) an anticancer antibiotic selected from among actinomycin D, idarubicin, doxorubicin, hydrarubicin, mitoxantrone and mitomycin C; and
(v) a platinum-based formulation selected from among carboplatin, cisplatin, nedaplatin and oxaliplatin.
(6) The antibody according to any one of (1) to (5), which is a human antibody or a humanized antibody.
(7) The antibody according to any one of (1) to (6), which comprises the amino acid sequence shown in any one of SEQ ID NOS: 1 to 3, 7 to 9, 13 to 15, 19 to 21 and 25 to 27, or an amino acid sequence substantially identical thereto, as each of a heavy chain first complementarity-determining region (VH CDR1), a heavy chain second complementarity-determining region (VH CDR2), or a heavy chain third complementarity-determining region (VH CDR3).
(8) The antibody according to any one of (1) to (7), which comprises the amino acid sequence shown in any one of SEQ ID NOS: 1 to 3, 7 to 9, 13 to 15, 19 to 21 and 25 to 27, or an amino acid sequence substantially identical thereto, as each of a heavy chain first complementarity-determining region (VH CDR1), a heavy chain second complementarity-determining region (VH CDR2), or a heavy chain third complementarity-determining region (VH CDR3), and which also comprises the amino acid sequence shown in any one of SEQ ID NOS: 4 to 6, 10 to 12, 16 to 18, 22 to 24 and 28 to 30, or an amino acid sequence substantially identical thereto, as each of a light chain first complementarity-determining region (VL CDR1), a light chain second complementarity-determining region (VL CDR2), and a light chain third complementarity-determining region (VL CDR3).
(9) The antibody according to any one of (1) to (8), which is selected from the following (i) to (v):
(i) an antibody comprising a heavy chain first complementarity-determining region (VH CDR1) consisting of the amino acid sequence shown in SEQ ID NO: 1, a heavy chain second complementarity-determining region (VH CDR2) consisting of the amino acid sequence shown in SEQ ID NO: 2, a heavy chain third complementarity-determining region (VH CDR3) consisting of the amino acid sequence shown in SEQ ID NO: 3, a light chain first complementarity-determining region (VL CDR1) consisting of the amino acid sequence shown in SEQ ID NO: 4, a light chain second complementarity-determining region (VL CDR2) consisting of the amino acid sequence shown in SEQ ID NO: 5, and a light chain third complementarity-determining region (VL CDR3) consisting of the amino acid sequence shown in SEQ ID NO: 6;

(ii) an antibody comprising a heavy chain first complementarity-determining region (VH CDR1) consisting of the amino acid sequence shown in SEQ ID NO: 7, a heavy chain second complementarity-determining region (VH CDR2) consisting of the amino acid sequence shown in SEQ ID NO: 8, a heavy chain third complementarity-determining region (VH CDR3) consisting of the amino acid sequence shown in SEQ ID NO: 9, a light chain first complementarity-determining region (VL CDR1) consisting of the amino acid sequence shown in SEQ ID NO: 10, a light chain second complementarity-determining region (VL CDR2) consisting of the amino acid sequence shown in SEQ ID NO: 11, and a light chain third complementarity-determining region (VL CDR3) consisting of the amino acid sequence shown in SEQ ID NO: 12;

(iii) an antibody comprising a heavy chain first complementarity-determining region (VH CDR1) consisting of the amino acid sequence shown in SEQ ID NO: 13, a heavy chain second complementarity-determining region (VH CDR2) consisting of the amino acid sequence shown in SEQ ID NO: 14, a heavy chain third complementarity-determining region (VH CDR3) consisting of the amino acid sequence shown in SEQ ID NO: 15, a light chain first complementarity-determining region (VL CDR1) consisting of the amino acid sequence shown in SEQ ID NO: 16, a light chain second complementarity-determining region (VL CDR2) consisting of the amino acid sequence shown in SEQ ID NO: 17, and a light chain third complementarity-determining region (VL CDR3) consisting of the amino acid sequence shown in SEQ ID NO: 18;

(iv) an antibody comprising a heavy chain first complementarity-determining region (VH CDR1) consisting of the amino acid sequence shown in SEQ ID NO: 19, a heavy chain second complementarity-determining region (VH CDR2) consisting of the amino acid sequence shown in SEQ ID NO: 20, a heavy chain third complementarity-determining region (VH CDR3) consisting of the amino acid sequence shown in SEQ ID NO: 21, a light chain first complementarity-determining region (VL CDR1) consisting of the amino acid sequence shown in SEQ ID NO: 22, a light chain second complementarity-determining region (VL CDR2) consisting of the amino acid sequence shown in SEQ ID NO: 23, and a light chain third complementarity-determining region (VL CDR3) consisting of the amino acid sequence shown in SEQ ID NO: 24; and (v) an antibody comprising a heavy chain first complementarity-determining region (VH CDR1) consisting of the amino acid sequence shown in SEQ ID NO: 25, a heavy chain second complementarity-determining region (VH CDR2) consisting of the amino acid sequence shown in SEQ ID NO: 26, a heavy chain third complementarity-determining region (VH CDR3) consisting of the amino acid sequence shown in SEQ ID NO: 27, a light chain first complementarity-determining region (VL CDR1) consisting of the amino acid sequence shown in SEQ ID NO: 28, a light chain second complementarity-determining region (VL CDR2) consisting of the amino acid sequence shown in SEQ ID NO: 29, and a light chain third complementarity-determining region (VL CDR3) consisting of the amino acid sequence shown in SEQ ID NO: 30.

(10) The antibody according to (7) or (8), which comprises a deletion, addition, substitution and/or insertion of one or several amino acids with respect to the amino acid sequence shown in any one of SEQ ID NOS: 1 to 3, 7 to 9, 13 to 15, 19 to 21, 25 to 27, 4 to 6, 10 to 12, 16 to 18, 22 to 24 and 28 to 30, and which has an activity of specifically reacting with human ITGA6B4.

(11) The antibody according to any one of (1) to (10), which is an antibody fragment selected from the group consisting of Fab, Fab', F (ab') 2, a single chain antibody (scFv), a dimerized V region (Diabody), a disulfide stabilized V region (dsFv), and a peptide comprising CDR.

(12) DNA encoding the antibody according to any one of (7) to (10).

(13) A recombinant vector comprising the DNA according to (12).

(14) A transformed cell line obtained by introducing the recombinant vector according to (12) into a host cell.

(15) A method for producing the antibody according to any one of (1) to (11), which comprises culturing the transformed cell line according to (14) in a medium, allowing the antibody according to any one of (1) to (11) to generate and accumulate in a culture, and collecting the culture from the culture.

(16) An inhibitor of cancer cell adhesion, which comprises the antibody according to any one of (1) to (11).

(17) An inhibitor of cancer cell adhesion, which comprises the antibody according to any one of (1) to (11), wherein when the inhibitor is used in combination with another anticancer agent, it is used to improve the sensitivity of a cancer cell to the anticancer agent.

(18) A pharmaceutical composition comprising the antibody according to any one of (1) to (11) and a pharmaceutically acceptable carrier.

(19) A pharmaceutical composition comprising the antibody according to any one of (1) to (11), wherein
in order to increase the drug sensitivity of a cancer cell and to inhibit the growth of the cancer cell and/or to kill the cancer cell, a patient who requires such action is provided with
(a) the antibody according to any one of claims 1 to 11, and
(b) an anticancer agent selected from among: an alkylating agent selected from among ifosfamide, nimustine hydrochloride, procarbazine hydrochloride, cyclophosphamide, dacarbazine and thiotepa; a metabolic antagonist selected from among cytarabine, enocitabine, gemcitabine hydrochloride, carmofur, tegafur and fluorouracil; a plant alkaloid selected from among etoposide, irinotecan, docetaxel, paclitaxel, vincristine, vindesine and vinblastine; an anticancer antibiotic selected from among actinomycin D, idarubicin, doxorubicin, hydrarubicin, mitoxantrone and mitomycin C; and a platinum-based formulation selected from among carboplatin, cisplatin, nedaplatin and oxaliplatin,
under conditions and in amounts, which are sufficient for the antibody to bind to the cancer cell, thereby causing inhibition of the growth of the cancer cell and/or the death of the cancer cell.

(20) The pharmaceutical composition according to (19), wherein the cancer cell has adhered to a bone marrow niche.

(21) The pharmaceutical composition according to (19) or (20), wherein the cancer is a solid cancer or a blood cancer.

(22) The pharmaceutical composition according to (21), wherein the solid cancer is lung cancer, colon cancer, stomach cancer, bladder cancer, pancreatic cancer, prostate cancer, hepatic cancer, cervical cancer, uterine cancer, ovarian cancer, breast cancer, head and neck cancer, or skin cancer.

(23) The pharmaceutical composition according to (21), wherein the blood cancer is leukemia, lymphoma, or myeloma.

According to the present invention, a method for inhibiting or treating cancer, which comprises administering the above-described antibody of the present invention to a subject, is further provided.

According to the present invention, a method for enhancing the effects of an anticancer agent, which comprises administering the above-described antibody of the present invention to a subject, is further provided.

According to the present invention, a method for inhibiting cell adhesion of cancer cells, which comprises administering the above-described antibody of the present invention to a subject, is further provided.

According to the present invention, use of the above-described antibody of the present invention for production of an inhibitor of cancer cell adhesion or a pharmaceutical composition, is further provided.

Effects of Invention

The antibody of the present invention is able to specifically recognize a human ITGA6B4 complex and specifically recognize a refractory cancer cell, which expresses an ITGA6B4 complex on the cell membrane thereof. The antibody of the present invention is also able to inhibit adhesion of cancer cells to a bone marrow niche, and enhance the effects of anticancer agents to anticancer agent resistant strains. Moreover, since the antibody of the present invention has the property of not affecting the growth of cells by itself, it is able to reduce unexpected effects, namely, side effects.

BRIEF DESCRIPTION OF DRAWINGS

The patent or application file contains at least one color drawing. Copies of this patent or patent application publication with color drawing will be provided by the USPTO upon request and payment of the necessary fee.

FIG. 3 shows that ITGB4 has been obtained as a result of the antigen identification with a mass spectrometer performed in Example 6. The present data consist of the output view obtained when the mass data obtained using a mass spectrometer (LCQ manufactured by Thermo) have been analyzed using the analysis software Mascot search (MATRIX SCIENCE).

FIG. 4 shows the results obtained by studying the reactivity of the IgG antibody produced in Example 3 with a purified soluble human ITGA6B4 antigen (Recombinant Human Integrin alpha 6 (X1) beta 4, R & D) according to ELISA.

FIG. 5 is a view showing that overexpression of α6-integrin (ITGA6) and β4 (ITGB4) has been identified by the comprehensive gene expression analysis of refractory leukemia.

FIG. 6 is a view showing that adhesion of leukemia cells via ITGA6/B4 is necessary for the leukemia cells to obtain resistance to anticancer agents. The figure shows that the anti-ITGA6/B4 antibody of the present invention contributes to attenuation of the adhesion ability.

FIG. 7 shows the results obtained by performing a cell adhesion inhibition test on four AML cell lines, namely, CSD/AML1, Kasumi3, MOLM1, and HNT34. The figure shows that the adhesiveness of the cells is reduced by administration of an anti-ITGA6/B4 antibody.

FIG. 9 shows the results obtained by examining the expression level of ITGA6B4 in leukemic stem cells.

FIG. 10 shows the results obtained by evaluating a change in the reactivity of antibodies in a gene expression inhibition test, where cells, into which ITGA6 and ITGB4 genes had been introduced by shRNA, were used.

FIG. 11 shows the results obtained by examining the infiltration-inhibiting effect by the combined use of an antibody and an anticancer agent, using vein transplant models. It has been demonstrated that the infiltration of leukemia cells into the bone marrow is significantly inhibited by administration of an anti-ITGA6BA antibody in both cases of a single administration and a combined use.

FIG. 12-1 shows the results obtained by examining the effect of an ITGA6B4 antibody to inhibit the in vitro growth of cells. In addition, in FIG. 12-2, the results are shown based on a cell growth level, in which PBS is defined as 100, and it has been demonstrated that the anti-ITGA6BA antibody does not have the effect of inhibiting cell growth when it is used alone.

FIG. 13 shows the in vivo antitumor effects by using vein transplant models. The extension of the survival rate was observed by the combined use of the antibody and the anticancer agent.

EMBODIMENTS FOR CARRYING OUT THE INVENTION

Figures 1, 2, 8:
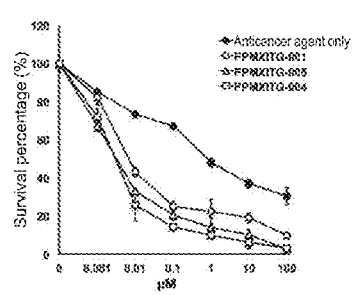
FIG. 1 shows two bands obtained as a result of the immunoprecipitation performed in Example 5.
FIG. 2 shows that ITGA6 has been obtained as a result of the antigen identification with a mass spectrometer performed in Example 6. The present data consist of the output view obtained when the mass data obtained using a mass spectrometer (LCQ manufactured by Thermo) have been analyzed using the analysis software Mascot search (MATRIX SCIENCE).
FIG. 8 shows influence caused by the combined use of an anti-ITGA6/B4 antibody with anticancer agents [AraC (cytarabine), DXR (doxorubicin), and VP16 (etoposide)]. It is found that the anti-ITGA6/B4 antibody enhances the effects of the anticancer agents.

Hereinafter, the present invention will be described more in detail. It is to be noted that, in the present description, there is a case where an integrin α6β4 complex that is an antigen specifically recognized by the antibody of the present invention may also be referred to as "ITGA6/B4," "ITGA6B4," "ITGA6B4 complex," "A6B4 complex," or the like.

The present inventors have conducted the pathological analysis of refractory leukemia, and as a result of a comprehensive gene expression analysis, the inventors have identified overexpression of α6-integrin (ITGA6) and β4 (ITGB4). Moreover, it has been found that this ITGA6/B4 is overexpressed, not only in EVI1 overexpression leukemia, but also in a group of patients with leukemia relapse after completion of the treatment (FIG. 5). Since this is a phenomenon generally observed in the refractory leukemia as a whole. It can be anticipated that this phenomenon will be particularly effective for the treatment of leukemia. According to the antibody of the present invention, the drug sensitivity of cancer showing resistance to the existing anticancer agents can be increased by inhibiting adhesion of the cancer cells to a bone marrow niche via ITGA6B4, and as a result, the effects of the anticancer agents can be restored or increased, and it becomes possible to carry out an effective treatment. With regard to the antibody of the present invention, an antibody, which particularly has high specificity and high affinity for the cancer cells of a patient and retains the effect of enhancing the aforementioned sensitivity to anticancer agents, is selected. Thus, high therapeutic effects on cancer cells can be obtained. The antibody of the present invention is characterized in that it is an antibody against an ITGA6B4 complex, in that it is able to carry out, in particular, the above-described "turn-out treatment", and in that it is able to significantly enhance the sensitivity of cancer cells to the existing anticancer agents. Although Patent Literature 1 describes the effects of integrin A6 or integrin B4 as a single use, the antibody of the present invention is an antibody against an integrin A6B4 complex. Since the antibody of the present invention recognizes integrin A6B4 and is modified to be an antibody suitable for the "turn-out treatment" proposed by the present invention, it can be anticipated that the present antibody will have significant therapeutic effects also on patients with leukemia relapse.

Unless otherwise specified in the present description, scientific terms used regarding the present invention have meanings that are generally understood by a person skilled in the art. In general, nomenclatures and techniques applied to the cell and tissue culture, molecular biology, immunology, microbiology, genetics, protein and nucleic acid chemistry, and hybridization, which are described in the present description, are well known in the present technical field, and thus, are commonly used.

The methods and techniques of the present invention are carried out in accordance with conventional methods that are well known in the present technical field, in such ways as described in a variety of general reference documents cited and discussed throughout the present description and more specific reference documents, unless otherwise specified.

Integrin A6B4 (ITGA6B4)

It has been known that integrin A6B4 (ITGA6B4) is a complex consisting of integrin α6 and integrin β4, and that the ITGA6B4 complex is associated with a large number of phenomena, such as interaction with an extracellular matrix, intercellular adhesion, adhesion of cells to tissues, and signaling. It has been known that integrin α6 forms a complex, not only with β4, but also with β1, so as to construct a complex referred to as "VLA6." The present antigen has been known as CD49f, and has been considered to be present in platelets or megakaryocyte and to be weakly expressed in a subpopulation of T cells. On the other hand, the complex as a target of the present study has been considered to be mainly expressed in normal cells of the bronchial epithelium, and also in the cancer cells of many cancers, including colon cancer as a typical example.

ITGA6B4 is not particularly limited in terms of structure, and thus, it totally means human ITGA6B4 including a monomer, a polymer, an intact form expressed on a cell membrane, a soluble form constituted in an extracellular region, a truncated form, a mutation form caused by genetic mutation, deletion, etc., and a form that has undergone posttranslational modification by phosphorylation or the like.

React and Reactivity

The terms "to react" and "reactivity" have the same meanings in the present description, unless otherwise specified. That is, these terms mean that an antibody recognizes an antigen. The antigen used herein may be any of an intact ITGA6B4 expressed on a cell membrane, a truncated form, and a soluble form. In addition, the antigen may be either an ITGA6B4 having a three-dimensional structure or a denatured ITGA6B4. Examples of a means for examining reactivity include flow cytometry (FACS), enzyme-linked immunosorbent assay (ELISA), Western blotting, microfluorescence measuring technique (FMAT), surface plasmon resonance (BIAcore), immunostaining, and immunoprecipitation.

The antibody used in flow cytometry may be either an antibody labeled with a fluorescent substance such as FITC or with biotin, or an unlabeled antibody. A fluorescently-labeled avidin, a fluorescently-labeled anti-human immunoglobulin antibody, or the like is used, depending on the presence or absence of labeling of the antibody used and the type thereof. Reactivity can be evaluated by adding a sufficient amount of anti-ITGA6B4 antibody (generally having a final concentration of 0.01 to 10 µg/mL) to an analyte, and then by comparing the obtained reactivity with the reactivity with a negative control antibody or a positive control antibody.

Antibody

In the present description, the following abbreviations (in the parentheses) are used in accordance with the customs, as necessary:

Heavy chain (H chain), light chain (L chain), heavy chain variable region (VH), light chain variable region (VL), and complementarity-determining region (CDR).

In the present description, the term "antibody" has the same definitions as immunoglobulin, and should be understood as generally known in the present technical field. Specifically, the term "antibody" is not limited by any given specific method for producing the antibody. For example, the term "antibody" includes, but is not limited to, a recombinant antibody, a monoclonal antibody, and a polyclonal antibody.

In the present description, the term "human antibody is used to mean any given antibody, in which the sequences of a variable region and a constant region are human sequences. This term includes antibodies which have human sequences and are modified, for example, to remove cysteine that may cause a possible decrease in immunogenicity, an increase in affinity, and undesirable folding. This term also includes antibodies produced in non-human cells by recombination, which enable glycosylation that is not specific to human cells. These antibodies can be prepared in various ways.

In the present description, the term "humanized antibody" means a non-human-derived antibody, in which amino acid residues characteristic for a non-human antibody sequence are substituted with residues found in corresponding positions of a human antibody. This "humanization" process is considered to reduce the immunogenicity of the obtained antibody in human. It would be understood that a non-human-derived antibody can be humanized using a technique well known in the present technical field. Please refer to, for example, Winter et al., Immunol. Today 14: 43-46 (1993). The target antibody can be produced by an engineering approach via a recombination DNA technique of substituting CH1, CH2, CH3, a hinge domain, and/or a framework domain with those of the corresponding human sequence. For example, WO92/02190, and U.S. Pat. Nos. 5,530,101, 5,585,089, 5,693,761, 5,693,792, 5,714,350 and 5,777,085 can be referred. In the present description, the term "humanized antibody" includes a chimeric human antibody and a CDR-grafted antibody, within the definitions thereof.

The sequence of a framework region (FR) in a variable region of the antibody of the present invention is not particularly limited, unless it substantially affects the specific binding ability of the antibody to the corresponding antigen. The FR region of a human antibody is preferably used, but it is also possible to use FR regions of animal species other than humans (e.g. a mouse, a rat, etc.).

In the present description, the term "phage antibody" is used to mean a scFv antibody generated from phage. That is, the phage antibody is an antibody fragment comprising the amino acid sequence of VH and VL. This fragment may comprise an amino acid sequence serving as a tag, as well as amino acids serving as a linker.

In one aspect, the antibody of the present invention comprises a constant region as well as a variable region (e.g. IgG antibody). The sequence of such a constant region is not particularly limited. For example, the constant region of a known human antibody can be used. The heavy chain constant region (CH) of a human antibody is not particularly limited, as long as it belongs to a human immunoglobulin (hereinafter referred to as "hIg"). Those of hIgG class are preferable, and any one of subclasses belonging to hIgG class, such as hIgG1, hIgG2, hIgG3 or hIgG4, may be used. On the other hand, the light chain constant region (CL) of a human antibody is not particularly limited, as long as it belongs to hIg, and those of κ class or λ class can be used. In addition, constant regions of animal species other than humans (e.g. a mouse or a rat) can also be used.

As the amino acid sequence of the variable region (CDR sequence and/or FR sequence) or constant region of the antibody of the present invention, the amino acid sequence of the original FR or constant region, from which the present antibody is derived, may be directly used. Otherwise, an amino acid sequence comprising a deletion, addition, substitution and/or insertion of one or several amino acids (for example, 1 to 8, preferably 1 to 5, more preferably 1 to 3, and particularly preferably one or two amino acids) may also be used, as long as the resulting antibody of the present invention can specifically recognize human ITGA6B4.

The antibody of the present invention preferably comprises the amino acid sequence shown in any one of SEQ ID NOS: 1 to 3, 7 to 9, 13 to 15, 19 to 21 and 25 to 27, as each of a heavy chain first complementarity-determining region (VH CDR1), a heavy chain second complementarity-determining region (VH CDR2), and a heavy chain third complementarity-determining region (VH CDR3), and it also comprises the amino acid sequence shown in any one of SEQ ID NOS: 4 to 6, 10 to 12, 16 to 18, 22 to 24 and 28 to 30, as each of a light chain first complementarity-determining region (VL CDR1), a light chain second complementarity-determining region (VL CDR2), and a light chain third complementarity-determining region (VL CDR3).

Moreover, the antibody of the present invention may also comprise an amino acid sequence that is substantially identical to the amino acid sequence shown in any one of SEQ ID NOS: 1 to 3, 7 to 9, 13 to 15, 19 to 21 and 25 to 27, as each of a heavy chain first complementarity-determining region (VH CDR1), a heavy chain second complementarity-determining region (VH CDR2), and a heavy chain third complementarity-determining region (VH CDR3), and it may further comprise an amino acid sequence that is substantially identical to the amino acid sequence shown in any one of SEQ ID NOS: 4 to 6, 10 to 12, 16 to 18, 22 to 24 and 28 to 30, as each of a light chain first complementarity-determining region (VL CDR1), a light chain second complementarity-determining region (VL CDR2), and a light chain third complementarity-determining region (VL CDR3).

The phrase "can specifically recognize human ITGA6B4" is used herein to mean that the antibody of the present invention has an activity of specifically reacting with human integrin A6B4, as with the antibody before modification. This antigen may be either intact ITGA6B4 expressed on a cell membrane, or a truncated form or a soluble form. Furthermore, the antigen may be either ITGA6B4 retaining a three-dimensional structure, or a denatured ITGA6B4. Examples of a means for examining binding activity include flow cytometry (FACS), enzyme-linked immunoadsorbent assay (ELISA), Western-blot, fluorescence microassay technology (FMAT), and surface plasmon resonance (BIAcore).

In the present invention, the phrase "as with the antibody before modification" does not necessarily mean the same level of activity. The activity may be increased, or the activity may also be decreased, as long as the antibody has the activity. An antibody having a decreased activity may be an antibody having an activity that is, for example, 30% or more, preferably 50% or more, more preferably 80% or more, further preferably 90% or more, and particularly preferably 95% or more of the activity of the original antibody.

The antibody of the present invention may comprise a substitution, deletion, addition and/or insertion of one or several amino acids with respect to the amino acid sequence of a variable region (a CDR sequence and/or an FR sequence), as long as it has an activity of specifically reacting with human integrin A6B4. As a method for preparing the amino acid sequence of an antibody specifically reacting with human integrin A6B4, which comprises a deletion, addition, substitution and/or insertion of one or several amino acids (for example, 1 to 8, preferably 1 to 5, more preferably 1 to 3, and particularly preferably 1 or 2 amino acids), a method of introducing a mutation into a protein has been well known to a person skilled in the art. For instance, such a skilled person could prepare a mutant antibody functionally equivalent to an antibody specifically reacting with human integrin A6B4 by appropriately introducing a mutation into the amino acid sequence of the aforementioned antibody according to a site-directed mutagenesis (Hashimoto-Gotoh, T, Mizuno, T, Ogasahara, Y, an DNA kagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, TA (1985) Rapid and efficient site-specific mutagenesis without phenotypic selection. Proc NAML Acad Sci USA. 82, 488-492), etc.

As such, an antibody, which comprises a mutation of one or several amino acids in a variable region thereof and specifically reacts with human integrin A6B4, is also included in the antibody of the present invention.

The antibody of the present invention is not limited by its origin, and it may be an antibody derived from any animal, such as a human antibody, a mouse antibody, or a rat antibody. Also, the present antibody may be a chimeric antibody or a humanized antibody.

The antibodies of the present invention may be different from one another in terms of amino acid sequence, molecular weight, isoelectric point, the presence or absence of a sugar chain or the form thereof, etc., depending on the after-mentioned cells or hosts that produce the antibodies, or a purification method. As long as the obtained antibody has an activity equivalent to the antibody of the present invention, it is included in the present invention. For example, an antibody that undergoes a modification after it has been translated to the amino acid sequence described in the present description is also included in the present invention. Moreover, an antibody that has undergone a posttranslational modification on a site other than those for the known posttranslational modification is also included in the present invention, as long as it has an activity equivalent to the antibody of the present invention. Furthermore, when the antibody of the present invention is allowed to express in prokaryotic cells such as *Escherichia coli*, a methionine residue is added to the N-terminus of the amino acid sequence of the original antibody. The antibody of the present invention includes such an antibody as well. An antibody that has undergone a posttranslational modification on a site other than those for the known posttranslational modification is also included in the present invention, as long as it has an activity equivalent to the antibody of the present invention.

Production of Antibody (1) Production of scFv Reacting with Antigen Using Phage Display Library The antibody of the present invention can be prepared by several methods known in the present technical field. For example, using a phage display technique, a library comprising a repertoire of antibodies having various affinity for ITGA6B4 can be provided. Subsequently, such a library can be screened to identify and isolate antibodies against ITGA6B4. Preferably, the phage library is a scFv phage display library that is generated using human VL and VH cDNA that has been prepared from mRNA isolated from human B cells. A method of preparing and screening such a library is known in the present technical field. A genetic substance is recovered from phage clones exhibiting reactivity that have been screened using a human ITGA6B4 as an antigen. By analyzing the selected phage gene, the DNA sequences of VH and VL encoding the variable region of a human antibody binding to the antigen can be determined. Using this scFv sequence, IgG is prepared from scFv, so as to obtain a human antibody.

(2) Preparation of IgG from scFv (Preparation of Human Antibody)

An H chain or L chain expression vector is produced, and it is then allowed to express in a host cell. Thereafter, the secreted supernatant is recovered and is then purified, so as to obtain a human antibody. Alternatively, such a human antibody can also be obtained by allowing VH and VL to express in a single vector (tandem type). These methods are well known, and can be carried out with reference to WO92/01047, WO92/20791, WO93/06213, WO93/11236, WO93/19172, WO95/01438, WO95/15388, WO97/10354, etc.

Specifically, DNA encoding VH is ligated to another DNA molecule encoding a heavy chain constant region (CH1, CH2 and CH3), so as to obtain a full-length heavy chain gene. The sequence of a human heavy chain constant region gene is known in the present technical field (for example, Kabat, E. A. et al., (1991) Sequences of Proteins of Immunological Interest, 5$^{th}$ edition, U. S. Department of Health and Human Services, NIH Publication No. 91-3242), and a DNA fragment including such a region can be obtained by standard PCR amplification. The heavy chain constant region may be the constant region of IgG1, IgG2, IgG3, IgG4, IgA, IgE, IgM or IgD. The most preferred constant region is that of IgG1 or IgG2. The constant region sequence of IgG1 may include any given various alleles or allotypes known to be generated among different individuals, such as Gm (1), Gm (2), Gm (3) or Gm (17). These allotypes correspond to a substitution of amino acids naturally-occurring in the constant region of IgG1.

DNA encoding VL is ligated to another DNA molecule encoding the light chain constant region CL, so as to obtain a full-length L chain gene (and a Fab light chain gene). The sequence of a human light chain constant region gene is known in the present technical field (for example, Kabat, E. A. et al., (1991) Sequences of Proteins of Immunological Interest, 5$^{th}$ edition, U. S. Department of Health and Human Services, NIH Publication No. 91-3242), and a DNA fragment including such a region can be obtained by standard PCR amplification. The light chain constant region may be the constant region of κ or λ. The κ constant region may include any given various alleles known to be generated among different individuals, such as Inv (1), Inv (2) or Inv (3). The λ constant region may be derived from any one of the three λ genes.

The thus obtained DNA encoding an H chain or L chain is inserted into a vector to produce an expression vector, and the produced expression vector is then allowed to express in a host cell. Thereafter, the secreted supernatant is recovered and purified to obtain a human antibody. Examples of the expression vector include a plasmid, retrovirus, adenovirus, adeno-associated virus (AAV), plant viruses such as cauliflower mosaic virus or tobacco mosaic virus, a cosmid, YAC, and EBV-derived episome. An expression vector and an expression regulatory sequence are selected, so that they are suitable for a host cell used for expression. An antibody light chain gene and an antibody heavy chain gene can be inserted into different vectors, or the two genes can also be inserted into a single expression vector. An antibody gene is inserted into an expression vector by a standard method (for example, ligation of a complementary restriction site on an antibody gene fragment to a vector, or blunt-ended ligation applied when no restriction sites are present).

A preferred vector encodes a functionally completed human CH or CL immunoglobulin sequence having a suitable restriction site, which has been produced by an engineering approach such that any given VH or VL sequence can be easily inserted and then expressed therein, as described above. In such a vector, splicing generally takes place between a splice donor site in the inserted J region and a splice acceptor site preceding a human C domain, or such splicing also takes place in a splice region existing in a human CH exon. Polyadenylation and transcription termination take place in a natural chromosomal site downstream of a coding region. A recombinant expression vector can also encode a signal peptide that promotes the secretion of an antibody chain derived from a host cell. An antibody chain gene can be cloned into a vector, such that a signal peptide can be ligated in-frame to the amino terminus of an immunoglobulin chain. The signal peptide may be either an immunoglobulin signal peptide or a heterogeneous signal peptide (namely, it may be a non-immunoglobulin protein-derived signal peptide).

An expression vector used for the antibody of the present invention may also have sequences such as a sequence for regulating replication of the vector in a host cell (e.g. a replication origin) or a selective marker gene sequence, in addition to an antibody gene and a regulatory sequence. The selective marker gene promotes selection of a host cell into which a vector has been introduced. For instance, the selective marker generally imparts resistance to drugs such as G418, hygromycin or methotrexate to a host cell into which the vector has been introduced. Preferred selective marker genes include a dihydrofolate reductase (DHFR) gene (used in methotrexate selection/amplification as a dhfr-host cell), a neomycin phosphotransferase gene (used in G418 selection), and a glutamate synthase gene.

A host cell is transformed with an antibody gene expression vector produced by the above-described method. Any type of cell may be used as a host cell, as long as it can produce the antibody of the present invention. Examples of such a host cell include bacteria, yeast, animal cells, insect cells, and plant cells. Among these cells, animal cells are preferable. Examples of the animal cells include Chinese hamster ovary cells CHO/dhfr(−) and CHO/DG44, monkey-derived cells COS (A. Wright & S. L. Morrison, J. Immunol. 160, 3393-3402 (1998)), and SP2/O cells (mouse myeloma) (K. Motmans et al., Eur. J. Cancer Prev. 5, 512-5199 (1996), R. P. Junghans et al., Cancer Res. 50, 1495-1502 (1990)). For transformation, a lipofectin method (R. W. Malone et al., Proc. NAML. Acad. Sci. USA 86, 6007 (1989), P. L. Feigner et al., Proc. NAML. Acad. Sci. USA 84, 7413 (1987)), an electroporation method, a calcium phosphate method (F. L. Graham & A. J. van der Eb, Virology 52, 456-467 (1973)), a DEAE-Dextran method, and the like are preferably applied.

A transformant is cultured, and a human antibody is then separated from the cells of the transformant or a culture medium thereof. For separation/purification of the antibody, methods such as centrifugation, ammonium sulfate fractionation, salting-out, ultrafiltration, affinity chromatography, ion exchange chromatography and gel filtration chromatography can be used by appropriately combining them.

Antigen-Binding Fragments

An antigen-binding fragment can be produced based on the antibody of the present invention, or based on the sequence information of a gene encoding the antibody of the present invention. Examples of the antigen-binding fragment include Fab, Fab', F(ab')$_2$, a single-chain antibody (scFv), a dimerized V region (Diabody), a disulfide stabilized V region (dsFv), and a peptide comprising a complementarity-determining region (CDR) derived from an antibody.

Fab is obtained by digesting IgG by papain in the presence of cysteine. It is an antibody fragment with a molecular weight of approximately 50,000, which is constituted with L chain and H chain variable regions, and an H chain fragment consisting of a CH1 domain and a portion of a hinge region. In the present invention, the above-described antibody can be obtained by papain digestion. In addition, Fab can also be prepared by incorporating DNA encoding a portion of the H chain and the L chain of the above-described antibody into a suitable vector, then performing transformation with the resulting vector, and then obtaining it from the transformant.

Fab' is an antibody fragment with a molecular weight of approximately 50,000, which is obtained by cleaving a disulfide bond between the H chains of the below-mentioned F(ab')$_2$. In the present invention, Fab' can be obtained by digesting the above-described antibody by pepsin, and then cleaving a disulfide bond with a reducing agent. In addition, as with Fab, Fab' can also be prepared by genetic engineering using DNA encoding the Fab'.

F(ab')$_2$ is obtained by digesting IgG by pepsin, and is an antibody fragment with a molecular weight of approximately 100,000, which is obtained by binding, via a disulfide bond, one fragment (Fab') constituted with L chain and H chain variable regions and an H chain fragment consisting of a CH1 domain and a portion of a hinge region, to the other fragment (Fab'). In the present invention, F(ab')$_2$ can be obtained by digesting the above-described antibody by pepsin. In addition, as with Fab, F(ab')$_2$ can also be prepared by genetic engineering using DNA encoding the F(ab')$_2$.

scFv is an antibody fragment obtained by ligating the C-terminus of one chain of Fv consisting of an H chain variable region and an L chain variable region to the N-terminus of the other chain thereof, using a suitable peptide linker, so as to form a single chain. (GGGGS)$_3$ having high flexibility can be used, for example, as such a peptide linker. For instance, DNA encoding the H chain variable region and L chain variable region of the above-described antibody and DNA encoding a peptide linker are used to construct DNA encoding a scFv antibody, and the thus constructed DNA is then incorporated into a suitable vector. Thereafter, scFv can be prepared from a transformant obtained by transformation with the aforementioned vector.

The dimerized V region (Diabody) is a dimer obtained by binding two fragments (e.g., scFv, etc.) to each other, each of which has been formed by binding a variable region to another variable region via a linker or the like. In general, Diabody comprises two VL regions and two VH regions. The bond between the fragments constituting the Diabody may be either a non-covalent bond or a covalent bond. It is preferably a non-covalent bond.

dsFv is a Fv fragment obtained by introducing a Cys residue into a suitable site in each of an H chain variable region and an L chain variable region, and then stabilizing the H chain variable region and the L chain variable region by a disulfide bond. The site in each chain, into which the Cys residue is to be introduced, can be determined based on a conformation predicted by molecular modeling. In the present invention, for example, a conformation is predicted from the amino acid sequences of the H chain variable region and L chain variable region of the above-described antibody, and DNA encoding each of the H chain variable region and the L chain variable region, into which a mutation has been introduced based on such prediction, is then constructed. The thus constructed DNA is incorporated into a suitable vector. Thereafter, dsFv can be then prepared from a transformant obtained by transformation with the aforementioned vector.

Further, it is also possible to ligate scFv antibody, dcFv antibody or the like using a suitable linker, or to fuse such an antibody fragment with streptavidin, so as to multimerize the antibody fragment.

Pharmaceutical Agent

According to the present invention, an inhibitor of cancer cell adhesion, which comprises the antibody of the present invention, and a pharmaceutical composition, which comprises the antibody of the present invention, are provided. In one embodiment, the present invention relates to the treatment of refractory leukemia, but is not limited thereto. Diseases caused by overexpression of an ITGA6B4 complex, other than refractory leukemia, can also be treated using the antibody of the present invention. Preferably, the therapeutic target is refractory leukemia. However, solid cancer (e.g. lung cancer, colon cancer, stomach cancer, bladder cancer, pancreatic cancer, prostate cancer, hepatic cancer, cervical cancer, uterine cancer, ovarian cancer, breast cancer, head and neck cancer, skin cancer, etc.), blood cancer (e.g. leukemia, lymphoma, myeloma, etc.), and the like are also included in the therapeutic target.

The inhibitor of cancer cell adhesion and the pharmaceutical composition, each of which comprises the antibody of the present invention, may comprise a pharmaceutically acceptable carrier, an excipient, a diluent, and the like, as appropriate. The inhibitor of cancer cell adhesion and the pharmaceutical composition of the present invention can be each formulated, for example, in the form of an injection. The applied doses of the inhibitor of cancer cell adhesion and the pharmaceutical composition of the present invention depend on the symptom degree, age and body weight of a patient, an administration method, and the like, and the weight of an antibody as an active ingredient is generally in the range of approximately 10 ng to approximately 100 mg/kg of body weight per day.

Detection of Cells

The antibody of the present invention, which has bound to cells, can be detected by flow cytometry, ELISA, or a combination thereof. As a device for detecting or quantifying cells, to which the antibody of the present invention has bound, a flow cytometer (FACS: Fluorescence Activated Cell Sorter) is preferable. Methods of using other measurement devices capable of measuring circulating tumor cells (CTC) may also be applied. Most preferably, cells, to which the antibody of the present invention has bound, can be measured using a flow cytometer. In this case, the antibody of the present invention has been preferably labeled with fluorescent dye. Blood cells obtained from a blood specimen are allowed to come into contact with the antibody of the present invention, which has been fluorescently labeled, and thereafter, the cells can be analyzed using a flow cytometer.

The present invention will be described more in detail in the following examples. However, these examples are not intended to limit the scope of the present invention.

EXAMPLES

Example 1: Screening for Phage Antibody Using Cancer Cell Line (1) Screening for Phage Antibody Bound to Cancer Cells (AML Line USCD-AML1)

USCD-AML1 cells (Oval et al., Blood 76: 1369-1374 (1990); Taetle et al., Cancer Res. 53: 3386-3393 (1993); Hu et al., Leukemia 10: 1025-1040 (1996)) were cultured by any given method. The cells were recovered and were then washed with cooled PBS. Thereafter, a human antibody phage library of $1\times10^{13}$ cfu (see JP Patent Publication (Kokai) No. 2005-185281 A, WO 2008/007648, and WO 2006/090750) was mixed with the resulting cells, and a reaction solution (1% BSA, 0.1% NaN3, and MEM) was then added thereto to a final volume of 1.6 mL. The obtained mixture was slowly rotated at 4° C. for 4 hours for performing a reaction. After completion of the reaction, the reaction solution was divided into two aliquots, and each aliquot was then layered on 0.6 mL of an organic solution (dibutyl phthalate and cycloheximide (9:1)) that had previously been prepared, and the thus obtained mixture was then centrifuged (3000 rpm) for 2 minutes using a microcentrifuge. Thereafter, the supernatant was discarded, and cells precipitated at the bottom of the tube were suspended in 0.7 mL of 1% BSA/MEM. Then, the obtained suspension was further layered on 0.7 mL of an organic solvent. Centrifugation was carried out in the same manner as described above, the supernatant was then discarded, and the cells were then suspended in 0.3 mL of PBS, followed by freezing with liquid nitrogen.

The frozen cells were thawed at 37° C., and were then infected with 20 mL of *Escherichia coli* DH12S (OD0.5) for 1 hour. The phage-infected *Escherichia coli* was placed in 600 mL of a 2×YTGA medium (2×YT, 200 μg/mL ampicisulfate, and 1% glucose), and it was then cultured at 30° C. overnight. Thereafter, 10 mL of the culture was placed in 200 mL of a 2×YTA medium (2×YT and 200 μg/mL ampicisulfate), and it was then cultured at 37° C. for 1.5 hours. Then, $1\times10^{11}$ helper phage KO7 was added to the culture, and the obtained mixture was further cultured at 37° C. for 1 hour. Subsequently, 800 mL of a 2×YTGAK medium (2×YT, 200 μg/mL ampicisulfate, 0.05% glucose, and 50 μg/mL kanamycin) was added to the culture, and the obtained mixture was then cultured at 30° C. overnight. Thereafter, the supernatant was recovered by centrifugation (8000 rpm) for 10 minutes. To the recovered supernatant, 200 mL of a PEG solution (20% polyethylene glycol 6000 and 2.5M NaCl) was added, and the obtained mixture was fully stirred. Thereafter, the reaction mixture was subjected to centrifugation (8000 rpm) for 10 minutes to precipitate phages. The phages were suspended in 10 mL of PBS. The obtained solution was defined as phages obtained from the $1^{st}$ screening.

Subsequently, the $2^{nd}$ screening was carried out. The cultured cells ($2\times10^{7}$) were mixed with the phages from the $1^{st}$ screening ($1\times10^{10}$), and a reaction solution (1% BSA, 0.1% NaN3, and MEM) was added to the mixture to a final volume of 0.8 mL. Thereafter, the same operations as those in the aforementioned $1^{st}$ screening were carried out, so as to obtain phages from the $2^{nd}$ screening.

The $3^{rd}$ screening was carried out using the phages ($1\times10^{9}$) obtained from the $2^{nd}$ screening in the same manner as described above.

(2) Analysis of Phage Antibodies

The phages obtained from the $3^{rd}$ screening were recovered, and the DNA sequences thereof were then analyzed by the existing method. Incomplete antibodies comprising deletions in the regions or antibodies having overlapping sequences were removed, so that phage antibodies each having an independent antibody sequence could be obtained (see Japanese Patent No. 4870348).

Example 2: Screening for Positive Phages by ELISA

Using a purified soluble human ITGA6B4 antigen (Recombinant Human Integrin alpha 6 (×1) beta 4, R & D), the reactivity of antigen-antibody was examined by ELISA. Specifically, the concentration of the soluble ITGA6B4 antigen was adjusted to be 10 μg/mL with PBS, and it was then added to Immuno Module/Strip Plates (NUNC) in an amount of 50 μL/well. It was left at rest at 37° C. for 2 hours. Thereafter, the soluble ITGA6B4 antigen was discarded, and a blocking solution (5% skimmed milk/0.05% NaN3/PBS) was added thereto in an amount of 200 μL/well, followed by performing blocking at 37° C. for 2 hours. Thereafter, the blocking solution was removed, and the residue was then washed with PBS. The culture supernatant of the above-mentioned phage from the second screening was added to each well in an amount of 100 μL/well, and it was then reacted at 37° C. for 1 hour. The resultant was washed with PBS five times, and 1 μg/mL Rabbit anti-cp3 that had been diluted with PBS/0.05% Tween 20 was then added to the resultant in an amount of 100 μL/well. The thus obtained mixture was reacted at 37° C. for 1 hour. The resultant was washed with PBS five times, and anti-Rabbit IgG (H+L)-HRP that had been 2000 times diluted with PBS/0.05% Tween 20 was further added to the resultant in an amount of 100 μL/well. The thus obtained mixture was reacted at 37° C. for 1 hour. The resultant was washed with PBS five times, and OPD in a 0.1 M citrate phosphate buffer (pH 5.1)+0.01% $H_2O_2$ was then added thereto in an amount of 100 μL/well. The obtained mixture was reacted at room temperature for 5 minutes. Thereafter, $2NH_2SO_2$ was added to the reaction solution in an amount of 100 μL/well, so as to terminate the coloring reaction. Subsequently, the absorbance at 492 nm was measured using SPECTRA max340PC (Molecular Devices). As a result, the DNA sequences of phage clones exhibiting a significant positive reaction with the soluble ITGA6B4 antigen were analyzed, and their CDR sequences were each confirmed, and those having an independent sequence were then classified. As a result, five antibodies having a particularly strong reactivity were selected, and they were referred to as PPMXITG-001 to -005.

With regard to PPMMTG-001 to -005, their heavy chain first complementarity-determining region (VH CDR1), heavy chain second complementarity-determining region (VH CDR2), heavy chain third complementarity-determining region (VH CDR3), light chain first complementarity-determining region (VL CDR1), light chain second complementarity-determining region (VL CDR2), and light chain third complementarity-determining region (VL CDR3) are shown below.

TABLE 1

|  | VH CDR1 | VH CDR2 | VH CDR3 | VL CDR1 | VL CDR2 | VL CDR3 |
| --- | --- | --- | --- | --- | --- | --- |
| PPMXITG-001 | SEQ ID NO: 1 | SEQ ID NO: 2 | SEQ ID NO: 3 | SEQ ID NO: 4 | SEQ ID NO: 5 | SEQ ID NO: 6 |
| PPMXITG-002 | SEQ ID NO: 7 | SEQ ID NO: 8 | SEQ ID NO: 9 | SEQ ID NO: 10 | SEQ ID NO: 11 | SEQ ID NO: 12 |
| PPMXITG-003 | SEQ ID NO: 13 | SEQ ID NO: 14 | SEQ ID NO: 15 | SEQ ID NO: 16 | SEQ ID NO: 17 | SEQ ID NO: 18 |
| PPMXITG-004 | SEQ ID NO: 19 | SEQ ID NO: 20 | SEQ ID NO: 21 | SEQ ID NO: 22 | SEQ ID NO: 23 | SEQ ID NO: 24 |
| PPMXITG-005 | SEQ ID NO: 25 | SEQ ID NO: 26 | SEQ ID NO: 27 | SEQ ID NO: 28 | SEQ ID NO: 29 | SEQ ID NO: 30 |

Example 3: Production of IgG Antibody from Phage Antibody (scFv)

(1) Production of Plasmid Expressing ITGA6B4 IgG Antibody

Formation of an IgG antibody from a phage antibody will be explained below, giving formation of an IgG antibody from ITGA6B4 as an example.

The VH and VL genes of the phage antibody (scFv) of ITGA6B4 are aligned in the order of VH-VL, and the VH and the VL are connected with each other via a linker having the following sequence, so as to have the structure of scFv.
<Linker Sequence>
Gly Gly Gly Gly Ser Gly Gly Gly Gly Ser Gly Gly Gly Gly Ser (SEQ ID NO: 31)

A human germline gene assumed to be used in the VH and VL of ITGA6B4 was searched on IMGT (*) (*IMGT: http://www.imgt.org), and a phage antibody was processed into an IgG antibody thereof, with reference to the search results of IMGT. The VH of ITGA6B4 was connected with the constant region of human IgG 1. With regard to the VL of ITGA6B4, the H chain and L chain genes, to which NheI was added to the 5' side thereof and EcoRI was added to the 3' side thereof, were totally synthesized by GenScript. The thus synthesized heavy chain and light chain genes were each incorporated into different expression vectors. That is to say, artificially synthesized genes of the H chain and the L chain were each cleaved with NheI and EcoRI, and the cleavages were then incorporated into the NheI and EcoRI sites of the expression vector pCAGGS, so as to obtain an anti-ITGA6B4 antibody H chain expression vector and an anti-ITGA6B4 L chain expression vector.

Expression vectors for other antibodies were produced by the same method as described above.
(2) Transient Expression of IgG Antibody FreeStyle (Life Technologies) was used for transient expression of an IgG antibody. 293-F (Life Technologies) used as floating cells for gene transfection was subcultured the day before transfection. On the day of transfection, 400 mL of a cell suspension whose cell density had been adjusted to be $1 \times 10^6$ cells/mL was prepared for the expression of one type of antibody. Solution I was prepared by suspending a total of 200 μg of plasmid consisting of 100 μg of an antibody heavy chain expression vector and 100 μg of an antibody light chain expression vector in OptiPro SFM. Subsequently, 200 μL of MAX reagent was added to 8 mL of OptiPRO (Solution II). Solution (I) was mixed with Solution (II), and the thus mixed solution was then left at rest at room temperature for 10 to 20 minutes. A total of 16 mL of the reaction solution was added to 400 mL of a 293 expression medium, in which the 293-F cells had been suspended, and the obtained mixture was then cultured at 37° C. in 8% $CO_2$ for 6 to 7 days, using a cell culture shaker TAITEC BioShaker BR-43FL. After 6 to 7 days of the culture, a culture supernatant containing each recombinant antibody was recovered, and this antibody was used as a material for purification.
(3) Purification of IgG Antibody The IgG antibody protein contained in the culture supernatant, which had been expressed above, was purified employing an Ab-Capcher ExTra (ProteNova) affinity column using AKTAprime. The obtained peak fraction was subjected to gel filtration using a Sephacryl S-300 column that had been equilibrated with Dulbecco's PBS as a solvent, so as to further purify it. The purified IgG antibody protein was quantified using an absorption coefficient. The absorption coefficient of the IgG antibody was calculated employing EXPASY ProtParam (http://web.expasy.org/protparam/), using total amino acid sequences of individual antibodies.
(4) Quantification of Anti-ITGA6B4 IgG Antibody by Enzyme-Linked Immunosorbent Assay (ELISA)

The concentration of an antibody contained in the culture supernatant of anti-ITGA6B4 IgG antibody-producing cells, which had been expressed and purified as described above, or the concentration of a purified antibody was quantified based on absorbance, and was also quantified by enzyme-linked immunosorbent assay (ELISA). As a solid-phase antibody, goat anti-human IgG (H+L) (which had previously been absorbed against mouse, rabbit, bovine, and mouse IgG) (COMSO BIO: American Qualex International, Inc.; AQI, Cat. No. A-110UD) was added in an amount of 100 μl/well (concentration: 5 μg/mL) to a plate, and it was then left at rest at 4° C. over a day and a night. Subsequently, Block Ace was added in an amount of 200 μL/well to the plate to block the antibody at room temperature for 1 hour. Thereafter, the antibody as a sample was subjected to serial dilution, and it was then added to each well, followed by incubation for 1 hour for performing a reaction. The reaction product was washed with PBST (0.05% Tween 20 and PBS) five times, and then, a detection antibody solution prepared by 10,000 times diluting goat anti-human IgG (H+L) (absorbed against mouse, rabbit, bovine, and mouse IgG)—HRP (COSMO BIO: AQI, Cat. A-110PD) with PBST was added in an amount of 100 μL/well to the resultant. The obtained mixture was incubated for 1 hour, and was then washed with PBST five times. Thereafter, a substrate buffer TMB was added in an amount of 100 μL/well to the resultant. The obtained mixture was incubated at room temperature in a dark place for 15 minutes, and a reaction termination solution was then added thereto in an amount of 100 μL/well so as to terminate the reaction. Thereafter, the absorbance at 450 nm was measured. Using purified human IgG as a standard product, a calibration curve was produced, and the concentration of a human antibody was calculated using this calibration curve.

Example 4: Reactivity of Anti-ITGA6B4 IgG Antibody with Cell Lines

The reactivity of the anti-ITGA6BA IgG antibody was examined using an ITGA6B4-expressing cell line, AML, cell line USCD-AML1. USCD-AML1 cells were recovered by centrifugation. The recovered cells were washed with PBS once, and the resulting cells were suspended in FACS Buffer (PBS containing 1% BSA, 2 mM EDTA, and 0.1% NaN3), resulting in a cell density of 1×10$^6$ cells/mL. 100 μL of this cell suspension was dispensed into a 96-well V bottom plate (Costar 3897). Thereafter, each ITGA6B4 IgG antibody was adjusted to be 0.02 to 2 μg/mL with FACS Buffer, and 100 μL of the prepared antibody solution was then added to the cells. The obtained mixture was incubated at 4° C. for 1 hour. Thereafter, the resulting cells were washed with FACS Buffer, and 100 μL of Alexa488-anti-human IgG (Invitrogen) solution that had been 750 times diluted with FACS Buffer was then added to the cells. The thus obtained mixture was further incubated at 4° C. for 1 hour. The resultant was washed by centrifugation with FACS Buffer twice, and was then equipped into HTS of FACS Calibur (BD), and the fluorescence intensity of FL1 in each well was measured. As a result, all of the antibodies (a: 10 ng/mL; b: 100 ng/mL; c: 1 μg/mL) exhibited strong reactivity with USCD-AML1. In addition, in order to examine whether the reactivity with a purified ITGA6B4 antigen did not disappear, ELISA was carried out by the same procedures as those of Example 2, and the reactivity was confirmed. An example thereof is shown in FIG. 4. As shown in FIG. 4, a clear positive reaction was obtained. As negative control antibodies, an anti-habu venom human IgG antibody, which had been produced by the same procedures as those for the concerned antibody, and a detection antibody only (described as "PBS"), were used. A representative example of the antibody described as "anti-ITGA6BA antibody" is PPMXITG-001.

Example 5: Immunoprecipitation Using Anti-ITGA6BA Antibody and High Expression Cell Line (1) Preparation of Solid-Phased Antibody Used for Immunoprecipitation First, the above-produced anti-ITGA6B4 antibody solution was dialyzed against a coupling buffer solution (0.1M NaHCO3-NaOH, pH9). Specifically, the antibody solution was enclosed within a dialysis membrane (Snake Skin Pleated Dialysis Tubing 10,000 MWCO), and this membrane was then immersed in 1.5 L of a coupling buffer solution (0.1M NaHCO3-NaOH, pH9). The solution was stirred at 4° C. for 2 to 3 hours using a stirrer, and the buffer solution was then exchanged with a fresh one, followed by performing a further dialysis for 2 to 3 hours. Thereafter, the buffer solution was exchanged with a fresh one again, and the dialysis was then carried out over a day and a night.

Subsequently, activated CNBr-activated Sepharose 4B to be used for solidification was prepared. Specifically, CNBr-activated Sepharose 4B manufactured by Amersham Biosciences was swollen with 1 mM HCl, and was then aspirated using an aspirator. To the resultant, 50 ml of a coupling buffer solution was added, and thereafter, the mixture was stirred and was then aspirated using an aspirator. While the mixture was aspirated, a coupling buffer solution was further added thereto.

Solidification of the antibody was carried out as follows. Specifically, 1 ml of activator gel was added to 5 mg of the antibody in 10 ml of the solution, and the obtained mixture was then reacted at room temperature for 2 hours. After completion of the reaction, the gel was transferred into a column, and was then washed with 1 ml of a coupling buffer solution ten times. Thereafter, the presence or absence of an unreacted antibody was confirmed by O.D. measurement. The solid-phased gel was replaced with 5 ml of a 0.2 M Glycine-NaOH solution (pH 8) twice, and 5 ml of the same solution as described above was then added thereto. The mixed solution was left at rest at room temperature for 2 hours, and the solution was then subjected to natural dripping. After that, 5 ml of 0.2 M Glycine-HCl (pH 3) was added thereto for replacement, and 5 ml of the same solution as described above was further added thereto. The obtained solution was left at rest for 5 minutes, followed by natural dripping Finally, the column was replaced with 20 ml of PBS, followed by natural dripping, and then, 1% NP40, a protease inhibitor, and 0.05% NaN$_3$/PBS were added to the resulting solution, so as to recover gel.

(2) Labeling of Protein on Cell Membrane with Biotin and Production of Cell Lysate A cultured hepatic cancer cell line was labeled with biotin as follows. Specifically, the cultured cells PC 14, which had been cultured to a cell count of approximately 10$^7$ to 10$^8$, were washed with PBS twice, and Collagenase I (manufactured by GIBCO), which had been adjusted to a concentration of 5 mg/ml with a cell dissociation buffer (manufactured by GIBCO), was then added to the resulting cells. The obtained mixture was reacted at 37° C. in a CO$_2$ incubator, so that the cells were released. Thereafter, the cells were recovered with a medium and were then washed with PBS(-) twice, and the number of cells was calculated using a hemocytometer. The cells were suspended in PBS(-), resulting in a concentration of approximately 5×10$^7$/ml. To this suspension, EZ-Link Sulfo-NHS-LC-Biotinylation Kit (PIERCE), which had been adjusted to 1 mg/ml with PBS, was added in an equal amount. The obtained mixture was left at rest at room temperature for 30 minutes, and was then washed with PBS twice.

A cell lysate was prepared from the biotin-labeled cells as follows. Specifically, 4 ml of a lysis buffer (a 1% NP40/detergent base solution, wherein the detergent base solution comprised 20 mM HEPES (pH 8.0), 140 mM NaCl, and a protease inhibitor) was added to the above-described biotin-labeled cells, so that the cells were suspended therein. The obtained suspension was placed in a Dounce homogenizer that had been cooled, and it was then homogenized. Thereafter, to the resulting solution, a detergent mix solution (1% NP40, tritonX-100, b-D-Maltoside, n-Octyl b-D-Glucoside, n-Octyl b-D-Maltoside, n-Decyl b-D-Maltoside, and deoxycholic acid, in each amount of 0.5%/detergent base solution) was added in a half amount (2 ml), and the obtained mixture was then subjected to rotation mixing at 4° C. for 4 hours. Thereafter, the mixed solution was centrifuged at 100,000 rpm for 30 minutes, and was then filtrated through a 0.22-μm filter MILLEX-GP.

(3) Immunoprecipitation Reaction

First, a solid-phased antibody (hereinafter referred to as "antibody beads") corresponding to approximately 60 µl (which was approximately 150 µl of solution) was placed in a 2-ml tube, and 4 mM biotin was then added in an amount of 1/10 volume (approximately 15 µl) to the tube. To this mixture, a lysate (600 µl) corresponding to a half culture dish that had been mixed with 60 µl of a biotin solution was added, and the thus obtained mixture was then reacted at 4° C. for several hours, while stirring. Thereafter, the tube was centrifuged (5500 g, 1 minute, 4° C.), and a supernatant was then removed. To the residue, 800 µl of a biotin/lysis-T buffer for washing (0.5 mM biotin, 0.1% Tween 20/PBS) was added, and the obtained mixture was then subjected to inversion mixing two or three times. The tube was centrifuged (5500 g, 1 minute, 4° C.), and a supernatant was then removed. This washing operation was carried out again, and 30 µl of a citric acid solution for elution (50 mM citric acid (pH 2.5)) was then added to the antibody beads, followed by stirring. Thereafter, the tube was centrifuged (5500 g, 1 minute, 4° C.), and a supernatant was then recovered. To the remaining antibody beads, 30 µl of a citric acid solution for elution was added again, followed by stirring, the obtained mixture was then centrifuged (5500 g, 1 minute, 4° C.), and a supernatant was recovered. This elution operation was further carried out repeatedly three times, and a sample solution was then recovered. To the recovered sample solution, 3 M Tris was added for neutralization. The obtained sample was electrophoresed by SDS-PAGE, and bands were then confirmed by silver staining. This sample was also subjected to Western-blot using streptavidin-HRP (Anti-Streptavidin, IgG Fraction, Conjugated to Peroxidase COR-TEX biochem), so that the biotinylated membrane protein bands were detected. As a result, as shown in FIG. 1, two bands were detected. The anti-ITGA6BA antibodies 1, 2 and 3 shown in FIG. 1 correspond to PPMXITG-001, 004 and 005, respectively.

Example 6: Mass Spectrometry Performed on Immunoprecipitated Bands (1) Trypsin Digestion in Gel A portion corresponding to the membrane protein detected in the above-described Example 5 was digested with trypsin in gel, so that a peptide was recovered. An SDS polyacrylamide gel electrophoresis was carried out according to an ordinary method, and a band obtained by staining with Coomassie brilliant blue was cut out. This band was immersed in a 200 mM ammonium bicarbonate-50% acetonitrile solution, and it was then shaken at 37° C. for 45 minutes. Thereafter, the solution was discarded, and the same operation as described above was repeated twice, so as to remove Coomassie brilliant blue. The resulting gel was dried under reduced pressure, and trypsin (20 µg/ml) dissolved in 40 mM ammonium bicarbonate (pH 8.1)-10% acetonitrile was then added to the gel in an amount of 4 µl per unit area (mm2) of a gel slice. The gel was left at room temperature for 1 hour, so that it was fully swollen. To the gel, a trypsin solution was added in an amount of 2.5 times the previously added trypsin solution, and the obtained mixture was then left at rest at 37° C. for 18 hours. Thereafter, the resultant was filtrated with a tube equipped with a filter having a pore size of 0.22 µm, so as to recover a peptide generated as a result of the cleavage of the antigen with trypsin.

(2) Identification of Antigen by Mass Spectrometry

The sample obtained by trypsin digestion in gel was subjected to HPLC, which was connected with an electrospray ionization ion trap quadrupole mass spectrometer. Individual peptides, which were successively eluted from a reverse phase chromatography column of the HPLC based on a difference in hydrophobicity as a result of changes in a linear concentration gradient of 0% to 80% acetonitrile comprising 0.1% TFA, were ionized by an electrospray method. Thereafter, the mass of each peptide was analyzed.

At the same time, the mass of the limited decomposition product of each peptide generated as a result of collision of the peptide with a helium atom placed on the midcourse of the flight path of ions was analyzed. When one amino acid is dissociated by limited decomposition, a smaller ion by the mass of the dissociated amino acid is observed. Thus, the type of the dissociated amino acid can be identified based on the mass difference. When another amino acid is dissociated, a smaller ion by the mass of the dissociated amino acid is observed. Thus, the type of the dissociated amino acid can be identified based on the mass difference. The internal amino acid sequence can be determined by conducting the same experimental data analysis as described above. A set of the obtained internal amino acid sequences was searched against the published amino acid sequence database, so as to identify the antigens. Consequently, it was demonstrated that the two bands obtained in Example 5 were ITGA6 (FIG. 2) and ITGB4 (FIG. 3).

Example 7: Analysis of Adhesion-Inhibiting Ability Using Anti-ITGA6/B4 Antibody

The ability of the anti-ITGA6/B4 antibody of the present invention to inhibit the adhesiveness of refractory leukemia cell lines was analyzed. As cell lines used as analysis targets, three cell lines, which highly express EVI1 as a marker molecule for refractory leukemia, were selected (UCSD/AML1, Kasumi-3, MOLM1, and HNT34).

A plate was coated with Matrigel (BD Bioscience) as a basement membrane matrix, so that an easy adhesive environment that was similar to a bone marrow niche was produced. A comparison was made among the cell lines, in terms of the adhesiveness of the cells treated with antibodies under the aforementioned conditions. As a result, it has become clear that the adhesiveness of the cells is decreased by addition of any of anti-ITGA6/B4 antibodies (PPMX-ITG-001, 004, and 005) (FIG. 6).

Example 8: Experiment for Examining Effects Obtained by Combined Use of the Antibody of the Present Invention with Anticancer Agent It has been anticipated that the anti-ITGA6/B4 antibody of the present invention enhances the effects of an anticancer agent. Hence, using the refractory leukemia cell lines UCSD/AML1, Kasumi3, MOLM1 and HNT34, the influence obtained by the combined use of the present antibody with anticancer agents commonly used for the treatment of leukemia, namely, AraC (cytarabine), DXR (doxorubicin) and VP16 (etoposide) was analyzed.

A comparison was made among the leukemia cell lines, in terms of their survival rate under conditions consisting of a single use of anticancer agent and the combined use of an anticancer agent and an antibody. As a result, it was confirmed that IC50 was clearly decreased by addition of the antibodies (PPMXITG-001, 004, and 005) (FIGS. 8-1 and 8-2). It is to be noted that FIG. 8-1 shows an example of the tests of examining combined effects, which were performed using DXR (doxorubicin) and AML1 cells.

From the obtained results, it was considered that the anti-ITGA6/B4 antibody has an action to enhance the effects of anticancer agents, and it was suggested that, by using the anti-ITGA6/B4 antibody, high effects can be obtained with the use of a smaller amount of anticancer agent. Moreover, it could be anticipated that side effects would be reduced by decreasing the effective dose of the anticancer agent.

REFERENCE (1) Alkylating agents:
ifosfamide, nimustine hydrochloride, procarbazine hydrochloride, cyclophosphamide, dacarbazine, thiotepa, etc.
(2) Metabolic antagonists:
cytarabine, enocitabine, gemcitabine hydrochloride, carmofur, tegafur, fluorouracil, etc.
(3) Plant alkaloids:
etoposide, irinotecan, docetaxel, paclitaxel, vincristine, vindesine, vinblastine, etc.
(4) Anticancer antibiotics:
actinomycin D, idarubicin, doxorubicin, hydrarubicin, mitoxantrone, mitomycin C, etc.
(5) Platinum-based formulations:
carboplatin, cisplatin, nedaplatin, oxaliplatin, etc.
Product names used in the description and abbreviation corresponding thereto:

AraC (cytarabine): This anticancer agent is mainly used for blood cancer. This is a first-line agent for acute myeloid leukemia.

DXR (doxorubicin): This anticancer agent is mainly used for lymphoma.

VP16 (etoposide): This anticancer agent is used for malignant lymphoma and acute leukemia.

UCSD/AML1: A cell line with a karyotype of t(3;3), which has been established in Taetel UCSD. It is derived from Caucasian.

Kasumi3: A cell line with a karyotype of t(3;7), which has been established at Hiroshima University. It is derived from Japanese.

MOLM1: A cell line with karyotypes of t(9;22) and inv(3), which has been established at Hayashibara Biochemical Lab., Inc. It is derived from Japanese.

HNT34: A cell line with a karyotype of t(3;3), which has been established at Tokyo Musashino Hospital. It is derived from Japanese.

Example 9: Analysis of Ability of Anti-ITGA6BA Antibody to Inhibit Cell Adhesion of AML1 Cell Lines An experiment was carried out to examine inhibition of cell adhesion of the four AML cell lines UCSD/AML1, Kasumi3, MOLM1 and HNT34. A plate was coated with Matrigel (BD Bioscience) as a basement membrane matrix, so that an easy adhesive environment that was similar to a bone marrow niche was produced. A comparison was made among the cell lines, in terms of the adhesiveness of the cells treated with antibodies.

Specifically, the anti-ITGA6B4 IgG antibody, which had been selected in Example 2, and had been then produced and evaluated in Examples 3 and 4, was used to 10000 cells/100 µL. The antibody was added to the cells to a final concentration of 0 to 10 µg/mL, and the obtained mixture was then incubated at 4° C. for 30 minutes. Thereafter, the reaction mixture was washed with RPMI 1640/10% FCS. Subsequently, the resultant was suspended in 100 µL of RPMI 1640/10% FCS, and the suspension was then added to each well of a 96-well plate coated with Matrigel (registered trademark). It was incubated at 37° C. for 2 hours, and was then washed with PBS three times. 90 µL of RPMI 1640/10% FCS and 10 µL of Cell counting kit 8 (manufactured by Dojindo Laboratories) were added to each well, and the mixture was then incubated at 37° C. for 30 minutes. Thereafter, measurement was carried out at a wavelength of 450 nm, using a spectrophotometer. As a control, an untreated cell line was used.

FIG. 7 is a graph showing the results of the aforementioned cell adhesion assay. As shown in FIG. 7, the adhesion ability of AML1 cells (the ratio of the number of adhering cells to the total number of cells) was significantly reduced by the addition of PPMXITG-001, PPMXITG-004, or PPM-MTG-005.

Example 10: Search of the Expression Level of ITGA6B4 in Leukemic Stem Cells

The expression pattern of the mRNA of ITGA6/B4 in healthy human subjects and leukemia patients was analyzed in accordance with the method described in Patent Literature 1. Using blood provided by refractory leukemia patients and volunteers, the expression of ITGA4/B1 (VLA4) and ITGA6/B4 in a hematopoietic stem cell fraction and in a leukemic stem cell fraction was confirmed. As a result, the data shown in FIG. 9 were obtained. The "HSC derived from healthy subjects" indicates a CD34+ fraction from normal samples (Hematopoietic Stem Cell: HSC), the "HSC derived from leukemia patients" indicates a CD34+ fraction from leukemia patient samples, and the "LSC derived from leukemia patients" indicates a CD34+CD38− fraction (leukemic stem cell fraction: LSC). By this search, it was confirmed again that the expression of ITGA6 and B4 is particularly high in the leukemic stem cells of leukemia patients, and thus that ITGA6 and B4 are useful as therapeutic targets.

Example 11: Evaluation of Reactivity of Antibody by Introduction of shRNA of ITGA6 and ITGB4 Genes In order to confirm that the antibody of the present invention reacts with an intact ITGA6B4 complex which is expressed on a cancer cell membrane, the reactivity of the antibody was evaluated, using cells into which shRNA of ITGA6 and ITGB4 genes had been introduced. Specifically, a UCSD/AML1 cell line was transfected with each of shITGA6 and shITGB4, which are small-hairpin RNAs (shRNAs) each having an activity of cleaving the mRNAs of ITGA6 and ITGB4 genes, so as to obtain cell lines, in which the expression of each gene was inhibited. Using the thus obtained cell lines, a change in the reactivity of the antibody was evaluated by FACS. Specific procedures for producing gene expression-inhibited cell lines using shRNA, and the test of examining the reactivity of the antibody by FACS were carried out in accordance with the methods described in Patent Literature 1 and Non Patent Literature 1.

Moreover, as commercially available ITGA6 and ITGB4 positive control antibodies, an anti-human ITGA6 rat antibody (Santa Cruz) and an anti-human ITGB4 mouse antibody (Millipore), which are described in Non Patent Literature 1, were used.

As a result, the following data shown in FIG. 10 were obtained. In the figure, the graph indicated as "untreated" means cells which have not undergone the shRNA treatment, the graph indicated as "control" means cells which have been treated only with a detection antibody <anti-human IgG-Alexa647 (Invitrogen)>, and the graphs indicated as shITGA6 and shITGB4 mean samples in which the expression of each gene has been inhibited by shRNA.

(1) Results of Gene Expression Inhibition by ShITGA6 (UCSD/AML1: ShITGA6)

As a result of the inhibition of the expression of ITGA6, the reactivity of the anti-ITGB4 positive control was not changed (D. BL-ITGB4), whereas the reactivity of the anti-ITGA6BA antibodies of the present invention almost disappeared (A. PPMXITG-001, B. PPMXITG-004, and C. PPMXITG-005).

(2) Results of Gene Expression Inhibition by ShITgb4 (UCSD/AML1: ShITgb4)

As a result of the inhibition of the expression of ITGB4, the reactivity of the anti-ITGA6 positive control was not changed (D. BLITGA6), whereas the reactivity of the anti-ITGA6BA antibodies of the present invention almost disappeared (A. PPMXITG-001, B. PPMXITG-004, and C. PPMXITG-005).

(3) Conclusion Regarding Expression Inhibition Tests, and Conclusion and Consideration Regarding Complex-Specific Recognition In the present example, the expression of ITGA6 and B4 in AML1 cells as analysis target cells was inhibited at an efficiency of approximately 50% to 60%. With regard to cells into which the expression inhibition has been successfully introduced, the cells are gated with GFP, so that only the expression-inhibited cells can be analyzed. Taking into consideration these matters, as described in (1) and (2) above, it was found that the antibody of the present invention lost its reactivity in both tests of examining the inhibition of the expression of ITGA6 and ITGB4. Also considering the results from Examples 2, 4 and 5, it was demonstrated that the antibody of the present invention recognizes only an ITGA6B4 complex, and does not recognize ITGA6 alone or ITGB4 alone.

Example 12: Verification of Therapeutic Effects of Antibody in Vein Transplant Models (Infiltration-Inhibiting Ability)

Using immunodeficient mice (NOG mice), vein transplant models of the refractory leukemia cell lines UCSD/AML1 and HNT34 were produced. The model mice were administered with a drug (AraC), an antibody, or the combined use thereof, and the effect of inhibiting bone marrow infiltration by such administration was then examined. After the leukemia cell line had been injected into mouse vein, the mice were administered with PPMXITG-005. Thereafter, the organ was removed from each experimental body, and the infiltration level of the human cells was then analyzed. Specifically, the removed organ was ground with a cell strainer (BD 352340), the separated cells were then obtained, and erythrocytes were then hemolyzed with a hemolytic agent (BD 555899). The cells ($1\times10^6$) were suspended in 100 µL of MACS Buffer (PBS(−) containing 2 mM EDTA and 5% BSA), and were then reacted with a human CD45 antibody (PE-label, BioLegend 304008), in order to identify the human cells. Thereafter, the resultant was washed with MACS Buffer three times, and was then evaluated with a flow cytometer (BD FACS Calibur).

Using infiltration of the leukemia cells into the bone marrow as an indicator, the medicinal effects obtained by the combined use of the developed antibody and the drug, or by the single use thereof, were evaluated. As a result, it was found that infiltration of the leukemia cells into the bone marrow was significantly inhibited by the combined use of the antibody and the drug or by the single use thereof. From these results, it is considered that inhibition of the adhesion of the leukemia cells to the bone marrow niche by the present antibody is useful for inhibiting the achievement of cell adhesion-dependent resistance to chemotherapy (FIG. 11).

Example 13: Effect of ITGA6B4 IgG Antibody to Inhibit In Vitro Cell Growth

ITGA6B4-expressing cells AML1 and SW480 were each prepared to a density of 1000 cells/well with a culture solution, and the obtained solution was then dispensed in an amount of 100 µL/well each, into a 96-well flat-bottom plate (NUNC 167008). The cells were cultured at 37° C. in the presence of 5% CO2 and 95% air for 24 hours. A 10 µg/mL ITGA6B4 antibody was produced, and 100 µL of the antibody was then added to the plate during the culture. The obtained mixture was further cultured at 37° C. in the presence of 5% CO2 and 95% air for 96 hours. After completion of the culture, 10 µL of Cell counting kit-8 (DOJIN CK04) was added to the culture, and while observing color development, the mixture was reacted at 37° C. in the presence of 5% CO2 and 95% air for several hours. Thereafter, using a plate reader, the absorbance at 450 nm was measured.

Growth rate=Absorbance of antibody-added well/
absorbance of antibody-not-added well×100%

Figures 1, 12:
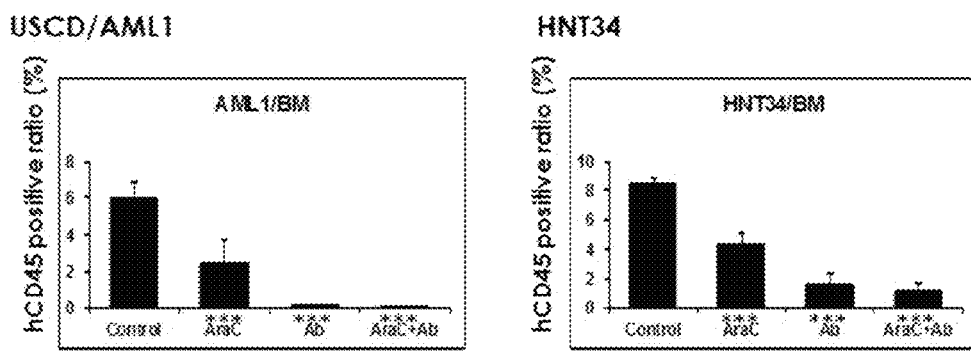
Figures 2, 12:
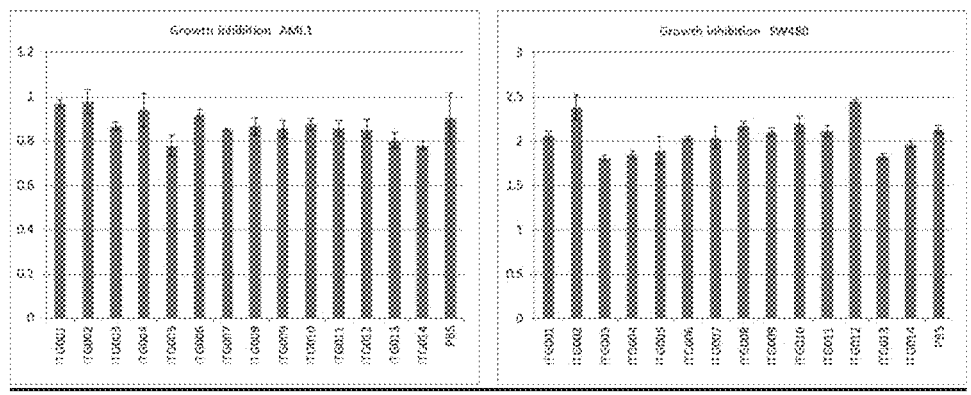

From these analysis results, the effect of each ITGA6B4 antibody to inhibit the cell growth was not observed (FIG. 12). These results demonstrate that the antibody alone does not have the medicinal effect of inhibiting the growth of cells, and thus, it is suggested that the antibody effectively acts regarding the reduction in side effects of the present invention.

Example 14: Test Regarding Combined Use of Antibody and Anticancer Agent Using Vein Transplant Models In order to confine the effects obtained by the combined use of the antibody and the drug in vivo, an experiment was carried out using vein transplant models. Two types of leukemia cell lines (UCSD/AML1 and HNT34) were each transplanted into severe immunodeficient mice (NOG mice: IL2RγKO mice) through the vein. Regarding experimental conditions, four conditions, namely, an untreated control, a single use of the anticancer agent, a single use of the antibody, and the combined use of the antibody and the anticancer agent, were determined and studied. Regarding administration conditions, the antibody was administered at a dose of 3 mg/kg once a week, the anticancer agent was administered at a dose of 150 mg/kg once a week, and the medicinal effects were examined based on the survival rate of n=5 for each condition. As a result, the control group and the single antibody administration group had the same survival rate, and the survival rate was increased in the single agent administration group. Moreover, in the combined use group in which the anticancer agent was used in combination with the antibody, significant extension of the survival rate was observed, in compared to the single use of the anticancer agent (FIG. 13).

Together with the results of Example 12 (FIG. 11), in which infiltration of leukemia cells into the bone marrow was analyzed after intravenous administration of the leukemia cells to mice, it has been considered that the antibody of the present invention has the following medicinal effects: (1)

the combined use of the antibody and an anticancer agent inhibits infiltration of leukemia cells that have been administered through the vein into the bone marrow; and (2) as a result, the increase of the survival rate is observed in mouse models. Accordingly, the usefulness of the antibody of the present invention has been demonstrated.

The invention claimed is:

1. An antibody which specifically recognizes a human integrin alpha6beta4 (ITGα6β4), wherein said antibody inhibits intercellular adhesion and is from the following:

(1) an antibody which comprises a heavy chain variable region having CDRs consisting of the heavy chain first complementarity determining region (VH CDR1) of SEQ ID NO: 1, the heavy chain second complementarity determining region (VH CDR2) of SEQ ID NO: 2, and the heavy chain third complementarity determining region (VH CDR3) of SEQ ID NO: 3, and a light chain variable region having CDRs consisting of the light chain first complementarity determining region (VL CDR1) of SEQ ID NO: 4, the light chain second complementarity determining region (VL CDR2) of SEQ ID NO: 5, and the light chain third complementarity determining region (VL CDR3) of SEQ ID NO: 6, (2) an antibody which comprises a heavy chain variable region having CDRs consisting of the heavy chain first complementarity determining region (VH CDR1) of SEQ ID NO: 7, the heavy chain second complementarity determining region (VH CDR2) of SEQ ID NO: 8, and the heavy chain third complementarity determining region (VH CDR3) of SEQ ID NO: 9, and a light chain variable region having CDRs consisting of the light chain first complementarity determining region (VL CDR1) of SEQ ID NO: 10, the light chain second complementarity determining region (VL CDR2) of SEQ ID NO: 11, and the light chain third complementarity determining region (VL CDR3) of SEQ ID NO: 12, (3) an antibody which comprises a heavy chain variable region having CDRs consisting of the heavy chain first complementarity determining region (VH CDR1) of SEQ ID NO: 13, the heavy chain second complementarity determining region (VH CDR2) of SEQ ID NO: 14, and the heavy chain third complementarity determining region (VH CDR3) of SEQ ID NO:15, and a light chain variable region having CDRs consisting of the light chain first complementarity determining region (VL CDR1) of SEQ ID NO: 16, the light chain second complementarity determining region (VL CDR2) of SEQ ID NO: 17, and the light chain third complementarity determining region (VL CDR3) of SEQ ID NO: 18, (4) an antibody which comprises a heavy chain variable region having CDRs consisting of the heavy chain first complementarity determining region (VH CDR1) of SEQ ID NO: 19, the heavy chain second complementarity determining region (VH CDR2) of SEQ ID NO: 20, and the heavy chain third complementarity determining region (VH CDR3) of SEQ ID NO: 21, and a light chain variable region having CDRs consisting of the light chain first complementarity determining region (VL CDR1) of SEQ ID NO: 22, the light chain second complementarity determining region (VL CDR2) of SEQ ID NO: 23, and the light chain third complementarity determining region (VL CDR3) of SEQ ID NO: 24, or (5) an antibody which comprises a heavy chain variable region having CDRs consisting of the heavy chain first complementarity determining region (VH CDR1) of SEQ ID NO: 25, the heavy chain second complementarity determining region (VH CDR2) of SEQ ID NO: 26, and the heavy chain third complementarity determining region (VH CDR3) of SEQ ID NO: 27, and a light chain variable region having CDRs consisting of the light chain first complementarity determining region (VL CDR1) of SEQ ID NO: 28, the light chain second complementarity determining region (VL CDR2) of SEQ ID NO: 29, and the light chain third complementarity determining region (VL CDR3) of SEQ ID NO: 30.

2. The antibody according to claim 1, which is an antibody fragment selected from the group consisting of Fab, Fab', F (ab') 2, a single chain antibody (scFv), a dimerized V region (Diabody).

3. An inhibitor of cancer cell adhesion, which comprises the antibody according to claim 1.

4. A pharmaceutical composition comprising the antibody according to claim 1.

5. A method for treating acute myeloid leukemia, comprising:
administering the pharmaceutical composition according to claim 4 to a subject in need thereof.

* * * * *